(12) United States Patent
Helal et al.

(10) Patent No.: US 11,124,529 B2
(45) Date of Patent: Sep. 21, 2021

(54) EUROPIUM BASED METAL ORGANIC FRAMEWORK FOR PALLADIUM SENSING

(71) Applicant: King Fahd University of Petroleum and Minerals, Dhahran (SA)

(72) Inventors: Aasif Helal, Dhahran (SA); Zain Hassan Abdallah Yamani, Dhahran (SA); Amir Al-Ahmed, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 16/502,557

(22) Filed: Jul. 3, 2019

(65) Prior Publication Data

US 2021/0002304 A1  Jan. 7, 2021

(51) Int. Cl.
*C07F 5/00* (2006.01)
*G01N 33/20* (2019.01)
*G01N 21/64* (2006.01)
*G01N 21/31* (2006.01)

(52) U.S. Cl.
CPC .............. *C07F 5/00* (2013.01); *G01N 21/314* (2013.01); *G01N 21/643* (2013.01); *G01N 33/20* (2013.01); *G01N 2021/3155* (2013.01); *G01N 2021/6432* (2013.01)

(58) Field of Classification Search
CPC ........ C07F 5/00; G01N 33/20; G01N 21/643; G01N 21/314; G01N 2021/3155; G01N 2021/6432
See application file for complete search history.

(56) References Cited

U.S. PATENT DOCUMENTS

| 10,175,175 B2 | 1/2019 | Azzazy et al. |
| 10,201,803 B2 | 2/2019 | Cohen et al. |

FOREIGN PATENT DOCUMENTS

| CN | 101585856 A | 11/2009 |
| CN | 107722289 A | 2/2018 |

OTHER PUBLICATIONS

Wen et al., Inorg. Chem. 2016, 55, 10114-10117 (Year: 2016).*
Cui et al., Biosensors and Bioelectronics 135 (2019) 208-215 (Year: 2019).*
Shi, et al. ; The roles of the allyloxy groups on terephthalate for the formation of three coordination networks ; Inorganic Chemistry Communications vol. 14, Issue 4 ; pp. 569-572 ; Apr. 2011 ; Abstract Only ; 2 Pages.
Zha, et al. ; Extraction of palladium from nuclear waste-like acidic solutions by a metal-organic framework with sulfur and alkene functions ; Journal of Materials Chemistry A, Issue 7 ; 2015 ; Abstract Only ; 5 Pages.
Helal, et al. ; An Ultrasensitive and Selective Metal-Organic Framework Chemosensor for Palladium Detection in Water ; Inorganic Chemsitry 58 ; pp. 1738-1741 ; 2019 ; 4 Pages.

* cited by examiner

*Primary Examiner* — Robert S Cabral
(74) *Attorney, Agent, or Firm* — Oblon, McClelland, Maier & Neustadt, L.L.P.

(57) ABSTRACT

A method of detecting $Pd^{2+}$ in an aqueous solution is described. The method involves mixing an Eu-based metal organic framework with the aqueous solution and measuring the amount of fluorescence quenching. The fluorescence quenching is specific to $Pd^{2+}$ and also allows a 44 ppb detection limit of $Pd^{2+}$. The Eu-based metal organic framework may be treated with a metal chelator and reused for sensitive detection of $Pd^{2+}$.

20 Claims, 12 Drawing Sheets

EUROPIUM BASED METAL ORGANIC FRAMEWORK FOR PALLADIUM SENSING

STATEMENT REGARDING PRIOR DISCLOSURES BY THE INVENTORS

Aspects of this technology are described in an article "An Ultrasensitive and Selective Metal-Organic Framework Chemosensor for Palladium Detection in Water" by Aasif Helal, Ha L. Nguyen, Amir Al-Ahmed, Kyle E. Cordova, and Zain H. Yamani, in *Inorganic Chemistry* 2019, 58, 31738-1741, DOI: 10.1021/acs.inorgchem.8b02871, which is incorporated herein by reference in its entirety.

BACKGROUND OF THE INVENTION

Technical Field

The present invention relates to a method of detecting palladium ion in a solution using a europium-based metal organic framework.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Palladium is well known for its use in a wide variety of industrial sectors—from electronic commodities, surgical instruments, and components in fuel cell technologies to catalysts in automobile exhaust systems. See Umemura, T.; Sato, K.; Kusaka, Y.; Satoh, H. Palladium, in: G. F. Nordberg, B. A. Fowler, M. Nordberg (Eds.), Handbook on the Toxicology of Metals, Academic Press, New York, 2015, pp. 1113-1123, Magano, J.; Dunetz, J. R. Chem. Rev. 2011; 111, 2177-2250, and Ruize-Castillo, P. and Buchwald, S. L. Chem. Rev. 2016, 116, 12564-12649, each incorporated herein by reference in their entirety.

Palladium as a rare transition metal has a wide spectrum of application in various industries like medical, jewelry, electrical, electronics, catalytic converters, and fuel cell industry as a homogeneous or heterogeneous catalyst and is one of the most important catalysts in vehicle exhaust catalyst systems. See Ruiz-Castillo, P.; Buchwald, S. L. Chem. Rev. 2016, 116, 12564-12649 and Omaye, S. T. Toxicology 2002, 180; 139-50, each incorporated herein by reference in their entirety.

Rapid industrialization has led to widespread pollution with heavy metals. The main sources of palladium pollution are catalytic converters of automobiles and from the residual palladium of synthetic intermediates in active pharmaceutical ingredients (APIs). Palladium at very low concentrations can have cytotoxic effects, and cause eye and skin allergies. See Liu, B.; Bao, Y.; Du, F.; Wang, H.; Tian, J.; Bai, R. Chem. Commun., 2011, 47, 1731. Moreover palladium ion can bind with thiol-containing amino acids, proteins, DNA and RNA and regulate various cellular processes. See Palladium, Environmental Health Criteria Series 226, International Programme on Chemical Safety, WHO, Geneva, 2002. Thus, the threshold for palladium in certain end products used by consumers is strictly limited from European Agency for the Evaluation of Medicinal Products (EMEA) to 5-10 ppm, and the proposed maximum dietary intake of palladium is less than 1.5-15 mg per day per person. See Li, H.; Fan, J.; Hu, M.; Cheng, G.; Zhou, D.; Wu, T.; Song, F.; Sun, S.; Duan C.; Peng, X. Chem.-Eur. J. 2012, 18, 12242.

The widespread use of palladium comes as a considerable risk of environmental pollution. See Kielhorn, J.; Melber, C.; Keller, D.; Mangelsdorf, I. Int. J. Hyg. Environ. Health 2002, 205, 417-432, Hosseini, M.-J.; Jafarian, I.; Farahani, S.; Khodadadi, R.; Tagavi, S. H.; Naserzadeh, P.; Mohammadi-Bardbori, A.; Arghavanifard, N. Metallomics 2016, 8, 252-259, Omaye, S. T. Toxicology 2002, 180, 139-150, Yusop, R. M.; Unciti-Broceta, A.; Johansoon, E. M. V.; Sanchez-Martin, R. M.; Bradley, M. Nat. Chem. 2011, 3, 239. To detect and assess palladium contamination, especially at low concentrations, there is a real need for an analytical process that is simple to operate, low in cost, highly sensitive, and provides real time monitoring. See Yang, Y.; Zhao, Q.; Feng, W.; Li, F. Chem. Rev. 2012, 113,192-270, Li, H.; Fan, J.; Peng, X. Chem. Soc. Rev. 2013, 42, 7943-7962, Tracey, M. P.; Pham, D.; Koide, K. Chem. Soc. Rev. 2015, 44, 4769-4791, each incorporated herein by reference in their entirety. The most effective strategy for achieving this is to design a fluorometric probe that takes advantage of palladium-catalyzed reactions or palladium coordination to N, O, S, or P-containing fluorogenic ligands. See Balamurugan, R.; Liu, J. -H.; Liu, B.-T. Coord. Chem. Rev. 2018, 376, 196-224, Luo, W.; Liu, W. J. Mater. Chem. B 2016, 4, 3911-5, Zhang, R.; Gao, M.; Bai, S.; Liu, B. J. Mater. Chem. B 2015, 3,1590-6, Gao, T.; Xu, P.; Liu, M.; Bi, A.; Hu, P.; Ye, B. Chem.-Asian J. 2015, 10,1142-5, Wang, M.; Liu, X.; Lu, H.; Wang, H.; Qin, Z. ACS Appl. Mater. Inter. 2015, 7, 1284-1289, each incorporated herein by reference in their entirety. However, the challenge here is that the majority of such chemosensors have poor selectivity/sensitivity or are irreversible, which prohibits their reuse. See Zhou, L.; Wang, Q.; Zhang, X.-B.; Tan, W. Anal. Chem. 2015, 87, 4503-7, Liu, F.; Du, J.; Xu, M.; Sun, G. Chem.-Asian J. 2016, 11, 43-8, Bhanja, A. K.; Mishra, S.; Saha, K. D.; Sinha, C. Dalton Trans., 2017,46, 9245-9252, each incorporated herein by reference in their entirety.

Several analytical methods have been developed for the detection of very low quantity of palladium species such as inductively coupled plasma mass spectrometry (ICP-MS), atomic absorption spectrometry (AAS), solid phase micro extraction-high performance liquid chromatography (SPME-HPLC), and X-ray fluorescence. See Dimitrova, B.; Benkhedda, K.; Ivanova, E.; Adams, F. J. Anal. At. Spectrom. 2004, 19, 1394-1396, incorporated herein by reference in its entirety. But these methods often require rigorous experimental conditions, complicated sample preparation steps, sophisticated instrumentation, and well-trained individuals. To meet this challenge for the rational design of palladium probe recent research activities on palladium detection have been focused onto fluorescent and colorimetric methods because of their operational simplicity, low cost, high selectivity and sensitivity, low detection limits and real time monitoring. See Tracey, M. P.; Pham, D.; Koide, K. Chem. Soc. Rev. 2015, 44, 4769-4791, incorporated herein by reference in its entirety. One of the popular strategies for designing a colorimetric or fluorescent probe for palladium is to take advantage of palladium-catalyzed reactions. See Yan, J.; Wang, X.; Zhou, L.; Zhang, L. RSC Adv. 2017, 7, 20369-72, incorporated herein by reference in its entirety. Furthermore, palladium can coordinate with the ligands containing N, O, S, or P which in combination of a chromogenic or fluorogenic group may result in a change in color or fluorescence. See Wang, M.; Yuan, Y.; Wang, H.; Qin, Z.; Analyst, 2016, 141, 832-5, incorporated herein by reference in its entirety. But these sensors are susceptible to external influences and are irreversible so they cannot be reused. Several MOF-based sensors have been reported for the detection of different metal ions. MOF-based $Pd^{2+}$ sensors were first reported by Zhengtao Xu et al. who prepared crystals of MOF-5 with pendant allyl thioether units which on binding with $Pd^{2+}$ produced a swift color change. See He, J.; Zha, M.; Cui, J.; Zeller, M.; Hunter, A. D.; Yiu S.-M.; Lee, S.-T.; Xu, Z. J. Am. Chem. Soc. 2013, 135, 7807-7810, incorporated herein by reference in its entirety. However, as mentioned by the author, the sensor suffers from instability, as is often observed for Zn-based MOFs. It was not stable in water and the sensor did not show any sensitive fluorogenic responses. Another luminescent Zn-MOF based on mixed linker that utilized the highly conjugated, rigid bpeb linker (bpeb=1,4-bis[2-(4-pyridy)pethenyl]benzene) in combination with a π-electron-rich tetra-topic carboxylate linker ($H_4$tcpb=1,2,4,5-tetrakis(4-carboxyphenyl)benzene), was reported by Sanjit Konar and co-workers. See Sanda, S.; Parshamoni, S.; Biswas, S.; Konar, S. Chem. Commun., 2015, 51, 6576-6579, incorporated herein by reference in its entirety. The luminescence of the MOF was quenched in the presence of $Pd^{2+}$ in DMF. But there was no application of this MOF in water. Recently two luminescent MOFs were reported by Eringathodi Suresh et al. for the sensing of the $Pd^{2+}$ employing, the Zn(II)/Cd(II)-based dual ligand luminescent metal-organic frameworks (LMOFs) with bipyridyl-based Schiff base, (E)-N'-(pyridin-4-ylmethylene) isonicotinohydrazide 2-aminoterephthalic acid as linkers. See Parmar, B.; Rachuri, Y.; Bisht, K. K.; Suresh, E. Inorg. Chem. 2017, 56, 10939-10949, incorporated herein by reference in its entirety. The LMOF produced quenching on combing with $Fe^{3+}/Pd^{2+}$ in water exhibiting a high sensitivity for $Pd^{2+}$ in aqueous condition but lacking of the selectivity as its luminescence is quenched both with the $Fe^{3+}$ and with $Pd^{2+}$. There is a need for preparation of the new MOF-based $Pd^{2+}$ sensor that can produce a high selectivity and sensitivity in water.

Metal-organic frameworks (MOFs) or porous extended crystalline framework have caused a revolution in coordination chemistry because of their versatility in synthetic methodology, structural modularity and tailorable features that originates from the functionalization of the secondary building units (SBUs) composing the opened 3-dimensional (3-D) framework including two components—the organic linkers and inorganic metal ion clusters. The highly porous and crystalline frameworks of MOFs endow them with potential practical applications such as gas storage and conversion, separation, drug delivery, catalysis, and sensing. See Trickett, C. A.; Helal, A.; Al-Maythalony, B. A.; Yamani, Z. H.; Cordova, K. E.; Yaghi, O. M. Nat. Rev. Mater. 2017, 2, 17045, Gándara, F.; Furukawa, H.; Lee, S.; Yaghi, O. M. J. Am. Chem. Soc. 2014, 136, 5271-5274, 2. (a) Qiu, S. L.; Xue, M.; Zhu, G. S. Chem. Soc. Rev. 2014, 43, 6116-6140. (b) Yin, H. M.; Wang, J. Q.; Xie, Z.; Yang, J. H.; Bai, J.; Lu, J. M.; Zhang, Y.; Yin, D. H.; Lin, J. Y. S. Chem. Commun. 2014, 50, 3699-3701, Vermeulen, N. A.; Karagiaridi, O.; Sarjeant, A. A.; Stern, C. L.; Hupp, J. T.; Farha, O. K.; Stoddart, J. F. J. Am. Chem. Soc. 2013, 135, 14916-14919, Misale, A.; Niyomchon, S.; Luparia, M.; Maulide, N. Angew. Chem., Int. Ed. 2014, 53, 7068-7073, Helal, A.; Qamaruddin, M.; Aziz, M. A.; Shaikh, M. N.; Yamani, Z. H. ChemistrySelect 2017, 2, 7630-7636, Jayaramulu, K.; Narayanan, R. P.; George, S. J.; Maji, T. K. Inorg. Chem. 2012, 51, 10089-10091, Hao, Z. M.; Song, X. Z.; Zhu, M.; Meng, X.; Zhao, S. N.; Su, S. Q.; Yang, W. T.; Song, S. Y.; Zhang, H. J. J. Mater. Chem. A 2013, 1, 11043-11050, each incorporated herein by reference in their entirety.

MOF-based lanthanides are often used for generating highly luminescent sensors but they have low absorbance and quantum yield due to Laporte selection rules. This problem is circumvented by complexation with a strongly absorbing linker. See Hao, Z. M.; Song, X. Z.; Zhu, M.; Meng, X.; Zhao, S. N.; Su, S. Q.; Yang, W. T.; Song, S. Y.; Zhang, H. J. J. Mater. Chem. A 2013, 1, 11043-11050, incorporated herein by reference in its entirety. In case of MOFs, this coupling leads to the direct energy transfers from the linker excited state to the metal energy level resulting in a large increase in the luminescence that is known as the "luminescence sensitization" or "antenna effect". See Sabbatini, N.; Guardigli, M.; Lehn, J.-M. Coord. Chem. Rev., 1993, 123, 201-228, incorporated herein by reference in its entirety. It is important that the energy of the triplet state of the organic linker should be properly tuned so that the proper transfer of energy from ligand to metal can be facilitated without any back transfer.

In designing new chemosensors for palladium detection, there are five criteria that must be met: (i) low energy, high wavelength fluorescence; (ii) selectivity for palladium over other potential contaminants; (iii) ability to operate with a low detection limit; (iv) reversibility such that the chemosensor can be regenerated; and (v) stability in aqueous media under different pH conditions. See Yang, Y.; Zhao, Q.; Feng, W.; Li, F. Chem. Rev. 2012, 113,192-270, Li, H.; Fan, J.; Peng, X. Chem. Soc. Rev. 2013, 42, 7943-7962, Tracey, M. P.; Pham, D.; Koide, K. Chem. Soc. Rev. 2015, 44, 4769-4791, Balamurugan, R.; Liu, J. -H.; Liu, B.-T. Coord. Chem. Rev. 2018, 376, 196-224, each incorporated herein by reference in their entirety. MOFs constructed from lanthanide-containing secondary building units (SBUs) can be stitched together by organic linkers with fluorogenic properties. See Cui, Y.; Yue, Y.; Qian, G.; Chen, B. Chem. Rev. 2012, 112, 1126-1162, Kreno, L. E.; Leong, K.; Farha, O. K.; Allendorf, M.; Duyne, R. P. V.; Hupp, J. T. Chem. Rev. 2012, 112, 1105-1125, Hu, Z.; Deibert B. J.; Li, J. Chem. Soc. Rev., 2014, 43, 5815-5840, each incorporated herein by reference in their entirety. In this way, direct energy transfer from appropriately designed organic linkers in their excited state to the lanthanide SBUs results in 'luminescence sensitization' and avoids the negative effects of Laporte selection rules that are common to lanthanide materials. See Rocha, J.; Carlos, L. D.; Paz, F. A. A.; Ananias, D. Chem. Soc. Rev., 2011,40, 926-940, Büinzli, J. C. G.; Eliseeva, S. V. Chem. Sci., 2013, 4, 1939-1949, each incorporated herein by reference in their entirety. Furthermore, the organic linkers can be functionalized with moieties that selectively and reversibly interact with palladium, even in environments where low concentrations are present. See Sanda, S.; Parshamoni, S.; Biswas, S.; Konar, S. Chem. Commun., 2015, 51, 6576-6579, Li, H.; Fan, J.; Hu, M.; G. Cheng, G.; Zhou, D.; Wu, T.; Song, F.; Sun, S.; Duan, C.; X. Peng, X. Chem. Eur. J., 2012, 18, 12242, each incorporated herein by reference in their entirety. In this way, the MOF backbone can be equipped with both recognition of palladium via coordinative binding and a fluorogenic site that correspondingly responds to this binding. Although MOFs have been designed with pyridinyl donors that effectively coordinate palladium, alkene functional groups are better suited due to their π-donor capabilities, which allow for selective and reversible coordination. See Parmar, B.; Rachuri, Y.; Bisht, K. K.; Suresh, E. Inorg. Chem. 2017, 56, 10939-10949, Doonan, C. J.; Morris, W.; Furukawa, H.; Yaghi, O. M. J. Am. Chem. Soc. 2009, 131, 9492-9493, Bloch, E. D.; Britt, D.; Doonan, C. J.; Uribe-Romo, F. J.; Furukawa, H.; Long, J. R.; Yaghi, O. M. J. Am. Chem. Soc. 2010, 132 14382-14384, Tu, T. T.; Nguyen, M. V.; Nguyen, H. L.; Yuliarto, B.; Cordova, K. E.; Demir, S. Coord. Chem. Rev. 2018, 364, 33-50; and He, J.; Zha, M.; Cui, J.; Zeller, M.; Hunter, A. D.; Yiu S.-M.; Lee, S.-T.; Xu, Z. J. Am. Chem. Soc. 2013, 135, 7807-7810, each incorporated herein by reference in their entirety.

One of the major challenges in developing and synthesizing an MOF that effectively takes up and interacts with a metal species selectively is the functionalization of the MOF pre-synthetically or post synthetically. A host network equipped with functional groups that specifically interact with the target analytes of the metal species and a chromogenic or fluorogenic site that responds to this binding may be needed. MOFs with pyridinyl donors are also known for Pd uptake, however the presence of alkene moieties in the linker could facilitate the selective sensing behavior towards $Pd^{2+}$ ions. See S. Cai, Y. Lu, S. He, F. Wei, L. Zhaoab and X. Zeng, Chem. Commun., 2013, 49, 822, incorporated herein by reference in its entirety.

In view of the forgoing, one objective of the present invention is to design and synthesize a new MOF chemosensor that meets the aforementioned criteria for palladium detection. A MOF is constructed using $Eu^{3+}$ and organic linkers that integrated allyloxy moieties to ensure a selective and reversible recognition site for palladium. The resulting MOF, termed KFUPM-3, is highly selective and sensitive to $Pd^{2+}$ and demonstrates regenerative properties. In particular an Europium-based MOF with 2,5-bis(allyloxy)terephthalic acid linker (BTA) was synthesized and studied for its $Pd^{2+}$ sensing properties in water.

BRIEF SUMMARY OF THE INVENTION

According to a first aspect, the present disclosure relates to a method of detecting $Pd^{2+}$ in an aqueous solution. The method involves the steps of mixing a Eu-based metal organic framework (Eu-MOF) with the aqueous solution to form a solution mixture. A fluorescence emission intensity of the solution mixture is measured while irradiating the solution mixture with a wavelength in a range of 320-350 nm. The fluorescence emission intensity is compared to a second fluorescence emission intensity of a substantially similar solution mixture that does not contain $Pd^{2+}$.

The Eu-MOF comprises $Eu^{3+}$ ion clusters where each $Eu^{3+}$ ion cluster has two $Eu^{3+}$ ions. Each $Eu^{3+}$ ion cluster is coordinated with a total of 6 linkers, and each linker has a dicarboxylic acid and two alkene groups.

In one embodiment, the alkene groups are part of allyloxy groups.

In one embodiment, the linker is 2,5-bis(allyloxy)terephthalic acid.

In one embodiment, the linker is present in the Eu-MOF with a weight percent in a range of 55-75 wt %, relative to a total weight of the Eu-MOF.

In one embodiment, each $Eu^{3+}$ ion cluster is coordinated in a 2D layered structure.

In a further embodiment, the 2D layered structure has an interlayer spacing in a range of 3.2-3.8 Å.

In one embodiment, the Eu-MOF has an average pore size in a range of 3.5-4.5 Å.

In one embodiment, the Eu-MOF has a pore volume in a range of 0.10-0.20 cm$^3$/g.

In one embodiment, the Eu-MOF has a BET surface area in a range of 200-250 cm$^2$/g.

In one embodiment, the Eu-MOF has an absolute quantum yield in a range of 0.43-0.53.

In one embodiment, the Eu-MOF is present in the solution mixture at a concentration in a range of 1-100 mM.

In one embodiment, the solution mixture has a pH in a range of 6.0-10.0.

In one embodiment, the method has a $Pd^{2+}$ limit of detection in a range of 10-60 ppb.

In one embodiment, the solution mixture further comprises at least one metal ion selected from the group consisting of $Ag^+$, $Pb^{2+}$, $Zn^{2+}$, $Mg^{2+}$, $Fe^{3+}$, $K^+$, $Co^{2+}$, $Al^{3+}$, $Fe^{2+}$, $Na^+$, $Cd^{2+}$, $Sr^{2+}$, $Rb^+$, $Cu^{2+}$, $Ni^{2+}$, $Hg^{2+}$, $Ga^{3+}$, $Cs^+$, $Ca^{2+}$, $Pt^{2+}$, $Ir^{3+}$, and $Rh^{3+}$.

In a further embodiment, the solution mixture comprises the at least one metal ion at a concentration in a range of 1-100 mM.

In one embodiment, the fluorescence emission intensity of the solution mixture is measured at a wavelength in a range of 605-630 nm.

According to a second aspect, the method further comprises the step of removing the Eu-MOF from the solution mixture to produce a recovered Eu-MOF. The recovered Eu-MOF is mixed with a solution comprising a metal chelator to produce a chelating solution. The Eu-MOF is separated from the chelating solution to produce a renewed Eu-MOF, and the Eu-MOF is reused for the detection of $Pd^{2+}$.

In one embodiment, the metal chelator is present in the chelating solution at a concentration in a range of 0.05-0.5 M.

In one embodiment, the metal chelator is EDTA.

In one embodiment, the renewed Eu-MOF is reused at least 3 times, and the renewed Eu-MOF has a fluorescence intensity that is at least 90% of the Eu-MOF fluorescence intensity before the mixing.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
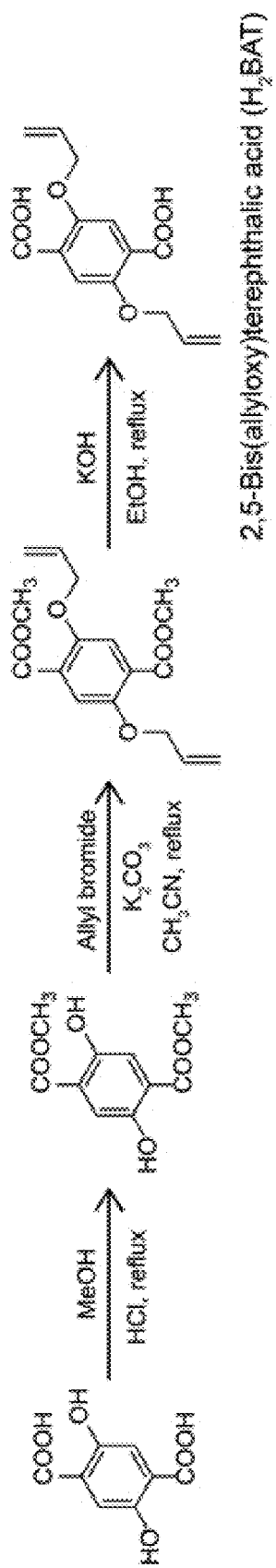
FIG. 1A shows the synthetic pathway for the functionalized organic linker, 2,5-bis(allyloxy)terephthalic acid (H$_2$BAT), used for designing a metal-organic framework chemosensor of the present disclosure.

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more." Within the description of this disclosure, where a numerical limit or range is stated, the endpoints are included unless stated otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the words "about," "approximately," or "substantially similar" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), or +/−20% of the stated value (or range of values). Within the description of this disclosure, where a numerical limit or range is stated, the endpoints are included unless stated otherwise. Also, all values and subranges within a numerical limit or range are specifically included as if explicitly written out.

As used herein, "compound" is intended to refer to a chemical entity, whether as a solid, liquid, or gas, and whether in a crude mixture or isolated and purified.

As used herein, "composite" refers to a combination of two or more distinct constituent materials into one. The individual components, on an atomic level, remain separate and distinct within the finished structure. The materials may have different physical or chemical properties, that when combined, produce a material with characteristics different from the original components. In some embodiments, a composite may have at least two constituent materials that comprise the same empirical formula but are distinguished by different densities, crystal phases, or a lack of a crystal phase (i.e. an amorphous phase).

The present disclosure is intended to include all hydration states of a given compound or formula, unless otherwise noted or when heating a material. For example, Ni(NO$_3$)$_2$, includes anhydrous Ni(NO$_3$)$_2$, Ni(NO$_3$)$_2$.6H$_2$O, and any other hydrated forms or mixtures. CuCl$_2$ includes both anhydrous CuCl$_2$ and CuCl$_2$.2H$_2$O.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium. Isotopes of carbon include $^{13}$C and $^{14}$C. Isotopes of nitrogen include $^{14}$N and $^{15}$N. Isotopes of oxygen include $^{16}$O, $^{17}$O, and $^{18}$O. Isotopes of nickel include $^{58}$Ni, $^{60}$Ni, $^{61}$Ni, $^{62}$Ni, and $^{64}$Ni. Isotopes of europium include $^{150}$Eu, $^{151}$Eu, $^{152}$Eu, $^{153}$Eu, $^{154}$Eu, and $^{155}$Eu. Isotopes of palladium include $^{100}$Pd, $^{102}$Pd, $^{103}$Pd, $^{104}$Pd, $^{105}$Pd, $^{106}$Pd, $^{107}$Pd, $^{108}$Pd, and $^{110}$Pd. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

For polygonal shapes, the term "diameter", as used herein, and unless otherwise specified, refers to the greatest possible distance measured from a vertex of a polygon through the center of the face to the vertex on the opposite side. For a circle, an oval, an ellipse, and a multilobe, "diameter" refers to the greatest possible distance measured from one point on the shape through the center of the shape to a point directly across from it.

As used herein, a metal organic framework (MOF) refers to compounds comprising metal ions or clusters coordinated to organic ligands to form one, two, or three dimensional structures. They are a subclass of coordination polymers and are often porous. The organic ligands included are sometimes referred to as "struts" or "linkers." More formally, a metal organic framework is a coordination network with organic ligands containing potential voids. As used herein, a coordination network is a coordination compound extending, through repeating coordination entities, in one dimension, but with cross-links between two or more individual chains, loops, or spirolinks, or a coordination compound extending through repeating coordination entities in two or three dimensions; and finally a coordination polymer is a coordination compound with repeating coordination entities extending in one, two, or three dimensions. In most cases, the pores are stable during elimination of guest molecules (often solvents) and metal organic frameworks may be used for the storage of gases such as hydrogen and carbon dioxide, gas purification, gas separation, catalysis, sensors, and supercapacitors.

The metal-organic framework described herein comprises metal ion centers which may be an ion of at least one metal selected from the group consisting of a transition metal (e.g. Sc, Ti, V, Cr, Mn, Fe, Co, Ni, Cu, Y, Zr, Nb, Mo, Tc, Ru, Rh, Pd, Ag, Hf, Ta, W, Re, Os, Ir, Pt, Au, Rf, Db, Sg, Bh, Hs, Mt, Ds, Rg, and Cn), a post-transition metal (e.g. Al, In, Ga, Sn, Bi, Pb, Tl, Zn, Cd, and Hg), and an alkaline earth metal (e.g. Be, Mg, Ca, Sr, Ba, and Ra). Further, the ion may be of any oxidation state $M^{+1}$, $M^{+2}$, $M^{+3}$, etc. In a preferred embodiment, the metal ion is an ion of at least one metal selected from the group consisting of Eu, Cu, Zn, Fe, Ni, Co, Mn, Cr, Cd, Mg, Ca, and Zr. In a more preferred embodiment, the metal ion is an ion of at least one metal selected from the group consisting of Eu, Zn, Ni, Mn, Cr, Cd, and Zr. In a preferred embodiment, the metal is Eu. The metal ion center is preferably $Eu^{3+}$, and the metal organic framework is called a europium-based metal organic framework, or Eu-MOF. The Eu-MOF may also be called KFUPM-3.

Generally, metal organic frameworks (MOFs) are composed of two major components, (i) a metal ion or cluster of metal ions and (ii) an organic molecule called a linker. These materials may often be referred to as hybrid organic-inorganic materials. The organic units are typically mono-, di-, tri-, or tetravalent ligands. The choice of metal and linker dictates the structure and properties of the MOF. For example, the metal's coordination preference influences the size and shape of pores by dictating how many linkers can bind to the metal and in which orientation. The linkers must meet certain requirements to form coordination bonds, primarily being multidentate, having at least two donor atoms (i.e. N—, O—, and/or S—) and being neutral or anionic. The structure of the metal organic framework is also affected by the shape, length, and functional groups present in the organic linker.

According to a first aspect, the present disclosure relates to a method of detecting $Pd^{2+}$ in an aqueous solution. The method involves the steps of mixing a Eu-based metal organic framework (Eu-MOF) with the aqueous solution to form a solution mixture.

In one embodiment, the aqueous solution may come from a body of water such as an ocean, a bay, a river, a spring, a lake, a swamp, or a pond or alternatively, from a treated artificial body of water, such as a pool, fountain, bath, aquarium, or hot tub. The sample may also be water taken from other natural environments such as groundwater (such as a well or an aquifer), rainwater, dew, fog, hot spring, a steam vent, snow, ice, or a geyser. In other embodiments, the aqueous solution may come from processed water or wastewater of industrial process including but not limited to a water treatment plant, a sewage treatment plant, a desalination plant, a manufacturing plant, a pharmaceutical plant, a chemical plant, a textile plant, a power plant, a gas station, a food processing plant (such as milk or fruit juice), a restaurant, a dry cleaner, or some other place that may be a source of contaminated water mixtures.

In one embodiment, the aqueous solution may be formed by mixing a solid or liquid compound with a volume of water. For instance, to test for levels of $Pd^{2+}$ in products, an amount of product, such as a foodstuff, cosmetic, or pharmaceutical compound, may be mixed with a volume of water to form an aqueous solution.

The Eu-MOF may be present in the solution mixture at a concentration in a range of 1-100 mM, preferably 5-80 mM, more preferably 7-60 mM, even more preferably 8-25 mM, or about 10 mM. Here, a formula weight of 2507.49 g/mol may be assumed, corresponding to the empirical formula $C_{90}H_{86}Eu_4N_2O_4$. In some embodiments, the Eu-MOF may be present at a concentration in a range of 0.01-10 mM, 0.1-5 mM, or 0.2-1 mM. In one embodiment, the Eu-MOF may be in the form of solid crystals or may be dissolved and/or dispersed in a liquid mixture immediately before being mixed together with the aqueous solution. The solution mixture may have a pH in a range of 6.0-10.0, preferably 6.5-9.5, more preferably 7.0-9.2.

The method next involves the step of measuring a fluorescence emission intensity of the solution mixture. The fluorescence emission intensity is measured while irradiating the solution mixture with one or more wavelengths in a range of 320-350 nm, preferably 322-345 nm, more preferably 325-340 nm, even more preferably 330-338 nm, or about 336 nm. In some embodiments, the solution mixture may be irradiated with one or more wavelengths in a range of 280-340 nm, preferably 290-330 nm.

In one embodiment, the fluorescence emission intensity may be measured in a fluorimeter. The fluorimeter may have an excitation light source such as an LED, a laser, a gas discharge lamp (such as a mercury vapor lamp, a xenon lamp, an argon lamp, or a metal halide lamp), and/or an incandescent bulb. The fluorimeter may use filters, dichroic filters, beam splitters, fiber optic cables, mirrors, reflectors, gratings, lenses, and diaphragms to manipulate the excitation light and the emitted light. In one embodiment, the emitted light may be detected at a substantially perpendicular angle to the path of the excitation light. The emitted light may be detected with a photodetector which comprises one or more of Si and/or InGaAs photodiodes, an avalanche photodiode, or a CCD.

In other embodiments, different optical properties may be measured of the solution mixtures, including but not limited to, polarization, Raman scattering, absorption, or dynamic light scattering.

The fluorescence emission intensity may be measured at a wavelength range of 575-585 nm, 585-595 nm, 605-630 nm, 645-650 nm, 685-690 nm, or 690-700 nm. In a related embodiment, the fluorescence emission intensity may be measured at a wavelength of 578, 592, 616, 648, or 695 nm.

In a preferred embodiment, the fluorescence emission intensity is measured at a wavelength range of 605-630 nm, preferably 610-625 nm, more preferably 612-622 nm, even more preferably 614-618 nm, or about 616 nm, which corresponds to a peak fluorescence emission.

In the method, the fluorescence emission intensity is compared to a second fluorescence emission intensity (at the same wavelength or wavelengths) of a substantially similar solution mixture that does not contain $Pd^{2+}$. The fluorescence emission intensity being lower than the second fluorescence emission intensity indicates the presence of $Pd^{2+}$ in the solution mixture, as the $Pd^{2+}$ quenches, or reduces, the fluorescence activity of the Eu-MOF. In one embodiment, the fluorescence quenching efficiency of $Pd^{2+}$ on the Eu-MOF is represented by a Stern-Volmer constant ($K_{sv}$) in a range of $1.0 \times 10^4$ $M^{-1}$-$50.0 \times 10^4$ $M^{-1}$, preferably $2.0 \times 10^4$ $M^{-1}$-$40.0 \times 10^4$ $M^{-1}$, more preferably $3.0 \times 10^4$ $M^{-1}$-$25.0 \times 10^4$ $M^{-1}$, even more preferably $5.0 \times 10^4 M^{-1}$-$15.0 \times 10^4 M^{-1}$, or about $7.8 \times 10^4 M^{-1}$.

In one embodiment, $Pd^{2+}$ may be detected with a limit of detection in a range of 10-60 ppb, preferably 15-55 ppb, more preferably 20-50 ppb, even more preferably 30-45 ppb, or about 44 ppb. In one embodiment, the method may involve a step of constructing a calibration curve to measure the amount of fluorescence quenching per known concentrations of $Pd^{2+}$. Then, a difference in fluorescence intensities between the solution mixture and a substantially similar solution mixture free of $Pd^{2+}$ may be used to determine a concentration of $Pd^{2+}$. In one embodiment, a 1 µM concentration of $Pd^{2+}$ may decrease a fluorescence intensity of the Eu-MOF by 5-10% compared to the fluorescence intensity of a substantially similar solution free of $Pd^{2+}$. In one embodiment, a 10 µM concentration of $Pd^{2+}$ may decrease a fluorescence intensity of the Eu-MOF by 40-60%. In one embodiment, a 100 µM-10 mM concentration of $Pd^{2+}$ may decrease a fluorescence intensity of the Eu-MOF by 90-98%. In one embodiment, a 100% decrease in the fluorescence intensity may denote complete fluorescence quenching, and may occur when a 2:1 $Pd^{2+}$:Eu-MOF molar ratio is reached, or if $Pd^{2+}$ beyond that ratio is present. In one embodiment, the Eu-MOF may detect palladium ion of oxidations states other than $Pd^{2+}$.

The Eu-MOF comprises $Eu^{3+}$ ion clusters where each $Eu^{3+}$ ion cluster has two $Eu^{3+}$ ions. However, in some embodiments, a Eu-MOF may be possible with $Eu^{3+}$ ions that are not clustered. Each $Eu^{3+}$ ion cluster is coordinated with a total of 4-8, preferably 6 linkers.

In one embodiment, each $Eu^{3+}$ ion cluster is coordinated in a 2D layered structure, and in a further embodiment, the 2D layered structure has an interlayer spacing in a range of 3.2-3.8 Å, preferably 3.3-3.7 Å, more preferably 3.4-3.6 Å, or about 3.5 Å. In one embodiment, each 2D layer may be in the form of a sql network with 4^4 tiling.

In one embodiment, each linker is a molecule with a dicarboxylic acid and two alkene groups. The linker may have a molecular weight in a range of 140-400 g/mol, preferably 145-350 g/mol, more preferably 200-325 g/mol, even more preferably 250-300 g/mol.

In one embodiment, the linker may be a benzene dicarboxylic acid with or without additional functional groups. The benzene dicarboxylic acid may be phthalic acid (benzene-1,2-dicarboxylic acid), isophthalic acid (benzene-1,3-dicarboxylic acid), terephthalic acid (benzene-1,4-dicarboxylic acid), or mixtures thereof. Preferably the benzene dicarboxylic acid is phthalic acid, and is functionalized with two alkene groups. In one embodiment, the alkene groups may be part of allyloxy groups. In a preferred embodiment, the linker is 2,5-bis(allyloxy)terephthalic acid.

In one embodiment, the linker may be present in the Eu-MOF with a weight percent in a range of 55-75 wt %, preferably 58-72 wt %, more preferably 60-68 wt %, or about 63 wt %, relative to a total weight of the Eu-MOF.

In one embodiment, the Eu-MOF may be in the form of needles or elongated rectangular prisms. The Eu-MOF in the form of elongated rectangular prisms may have a length in a range of 5-50 µm, preferably 10-45 µm, more preferably 15-40 µm, and a thickness and width in a range of 1-4 µm, preferably 1.5-3.5 µm. The Eu-MOF may be elongated with an aspect ratio (length:width) in a range of 20:1-8:1, preferably 18:1-12:1. In other embodiments, the Eu-MOF may be in the form of particles with a spherical shape, or may be shaped like cylinders, boxes, spikes, flakes, plates, ellipsoids, toroids, stars, ribbons, discs, rods, granules, prisms, cones, flakes, platelets, sheets, or some other shape.

In one embodiment, the Eu-MOF has a pore volume in a range of 0.10-0.20 $cm^3/g$, preferably 0.11-0.19 $cm^3/g$, more preferably 0.12-0.18 $cm^3/g$, even more preferably 0.13-0.17 $cm^3/g$ or about 0.159 $cm^3/g$.

In one embodiment, the Eu-MOF has a BET surface area in a range of 200-250 $cm^2/g$, preferably 205-245 $cm^2/g$, more preferably 210-240 $cm^2/g$, even more preferably 215-235 $cm^2/g$, or about 227 $cm^2/g$.

In one embodiment, the Eu-MOF has an absolute quantum yield in a range of 0.40-0.55, preferably 0.42-0.53, more preferably 0.45-0.50, or about 0.48. Here, the absolute quantum yield may be measured with one or more fluorescence excitation wavelengths in any of the ranges as previously described and by observing fluorescence emission at one or more wavelengths in any of the ranges as previously described.

In one embodiment, the solution mixture further comprises at least one metal ion selected from the group consisting of $Ag^+$, $Pb^{2+}$, $Zn^{2+}$, $Mg^{2+}$, $Fe^{3+}$, $K^+$, $Co^{2+}$, $Al^{3+}$, $Fe^{2+}$, $Na^+$, $Cd^{2+}$, $Sr^{2+}$, $Rb^+$, $Cu^{2+}$, $Ni^{2+}$, $Hg^{2+}$, $Ga^{3+}$, $Cs^+$, $Ca^{2+}$, $Pt^{2+}$, $Ir^{3+}$, and $Rh^{3+}$. In a preferrred embodiment, the solution mixture further comprises at least one metal ion selected from the group consisting of $Ag^+$, $Pb^{2+}$, $Zn^{2+}$, $Mg^{2+}$, $Fe^{3+}$, $K^+$, $Co^{2+}$, $Al^{3+}$, $Fe^{2+}$, $Na^+$, $Cd^{2+}$, $Sr^{2+}$, $Rb^+$, $Cu^{2+}$, $Ni^{2+}$, $Hg^{2+}$, $Ga^{3+}$, $Cs^+$, and $Ca^{2+}$. In a more preferred embodiment, the solution mixture further comprises at least one metal ion selected from the group consisting of $Ag^+$, $Pb^{2+}$, $Co^{2+}$, $Cd^{2+}$, $Sr^{2+}$, $Rb^+$, $Ni^{2+}$, $Hg^{2+}$, $Ga^{3+}$, and $Cs^+$. The at least one metal ion may be present in the solution mixture at a concentration in a range of 1-100 mM, preferably 2-80 mM, more preferably 5-60 mM, even more preferably 7-50 mM, or about 10 mM. In some embodiments, the at least one metal ion may be present at higher concentrations, such as 50 mM-2 M, 100 mM-1 M, or 0.2 M-0.5 M. Here, the at least one metal ion may be present without changing the detection limit of $Pd^{2+}$ in the solution mixture, in other words, the at least one metal ion does not interfere with the ability of $Pd^{2+}$ to quench or decrease the fluorescence activity of the Eu-MOF. In other embodiments, the presence of the at least one metal ion may interfere and increase the detection limit of the method by a factor of at least 1.1, at least 1.5, at least 5, or at least 10.

In other embodiments, the solution mixture may comprise two or more of the metal ions from the group mentioned above. For instance, the solution mixture may comprise two metal ions that have a mass ratio with each other in a range of 1:100-100:1, preferably 1:10-10:1, or 1:4-4:1.

According to a second aspect, the method further comprises the step of removing the Eu-MOF from the solution mixture to produce a recovered Eu-MOF. The recovered Eu-MOF is mixed with a solution comprising a metal chelator to produce a chelating solution. The Eu-MOF is separated from the chelating solution by centrifugation, filtering, or decanting to produce a renewed Eu-MOF. The renewed Eu-MOF may be rinsed with water and/or an organic solvent, such as ethanol. The Eu-MOF is reused for the detection of $Pd^{2+}$.

In one embodiment, the metal chelator is present in the chelating solution at a concentration in a range of 0.05-0.5 M, preferably 0.07-0.4 M, more preferably 0.08-0.2 M, or about 0.1 M. The metal chelator may be ethylenediaminetetraacetic acid (EDTA), ethylene glycol-bis(β-aminoethyl ether)-N,N,N',N'-tetraacetic acid (EGTA), iminodisuccinic acid (IDS), polyaspartic acid, ethylenediamine-N,N'-disuccinic acid (EDDS), methylglycinediacetic acid (MGDA), L-glutamic acid N,N-diacetic acid tetrasodium salt (GLDA). In one embodiment, the metal chelator is EDTA.

In one embodiment, the renewed Eu-MOF is reused at least 1 time, at least 2 times, more preferably at least 3 times, and the renewed Eu-MOF has a fluorescence intensity that is at least 90%, preferably at least 92%, more preferably at least 95%, even more preferably at least 97% of the Eu-MOF fluorescence intensity before the mixing.

The examples below are intended to further illustrate protocols for preparing, characterizing the europium-based metal-organic framework and uses thereof, and are not intended to limit the scope of the claims.

Example 1

Synthesis

Figure 1B:
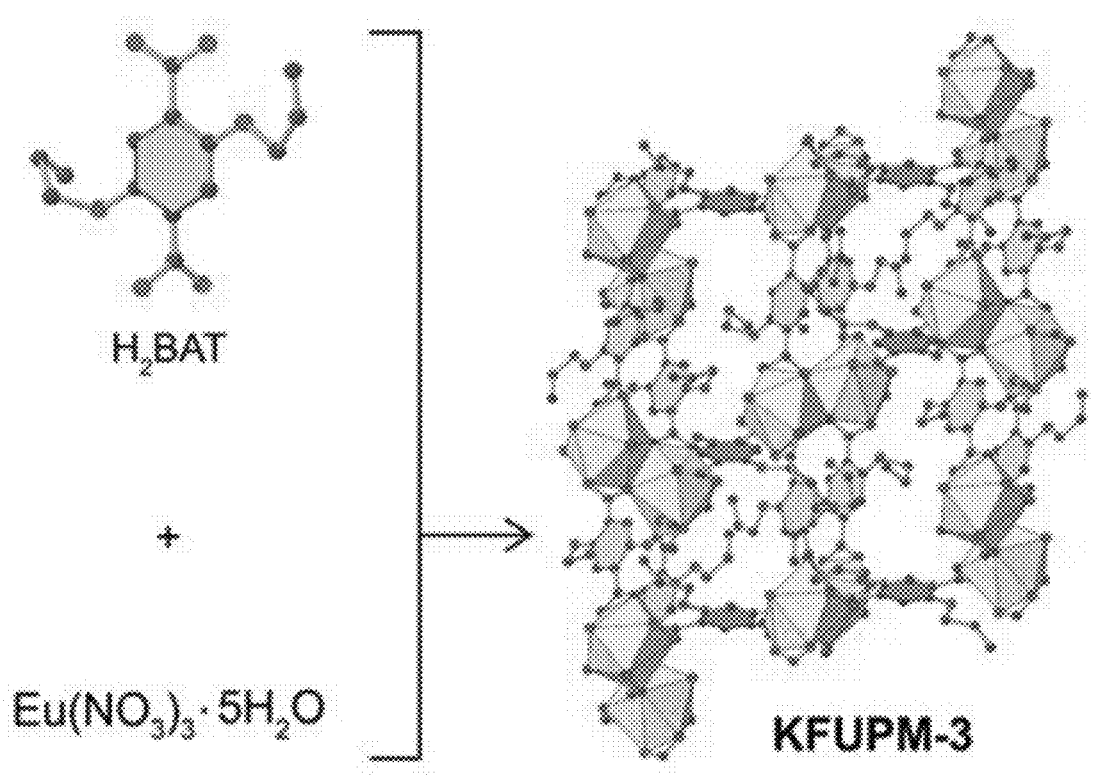
FIG. 1B illustrates the single crystal structure of KFUPM-3 constructed from BAT$^{2-}$ and Eu$^{3+}$ building blocks.

The first step in realizing a new MOF chemosensor centered on designing a linker that was capable of selectively binding palladium. After protecting the carboxylic acid of the commercially available, 2,5-dihydroxyterephthalic acid, a Williamson ether synthesis was performed to introduce allyloxy groups at the 2 and 5 positions of the terephthalic acid (FIG. 1A), which is confirmed by the doublet peaks at 4.57, 5.21, 5.41, and multiplet peak at 6.02-5.95 in the $^1$H NMR. This was followed by a saponification to deprotect the allyloxy-functionalized linker in order to achieve the targeted 2,5-bis(allyloxy)terephthalic acid ($H_2$BAT, or $H_2$L) in 85% yield (FIG. 1A). The synthesized $H_2$BAT was fully characterized by nuclear magnetic resonance ($^1$H and $^{13}$C NMR) and elemental analysis. With $H_2$BAT in hand, the MOF synthesis was then performed under solvothermal conditions. Specifically, $Eu(NO_3)_3 \cdot 5H_2O$ and $H_2$BAT were dissolved in a 5:2:1 v:v solution of N,N'-dimethylformamide, ethanol, and water, respectively, and the resulting solution was heated at 80° C. for 3 d to produce KFUPM-3 as colorless, rhombohedral-shaped single crystals (FIG. 1B).

Example 2

Synthesis of 2,5-Bis(allyloxy)terephthalic acid ($H_2$L)

A solution of 2,5-dihydroxyterephthalic acid (500 mg, 2.5 mmol) in methanol (10 mL) and 2 drops of HCl was refluxed for 10 h. The solvent was removed under vacuum and the residue was diluted with water and extracted with $CH_2Cl_2$. The organic layer was dried over anhydrous $Na_2SO_4$ and concentrated. The residue was purified by $SiO_2$ column chromatography (elution with ethyl acetate:hexane in 1:2 v:v) to give A in 87% yield. A mixture of A (450 mg, 2.0 mmol), allyl bromide (530 mg, 4.4 mmol), potassium carbonate (1098 mg, 8.0 mmol) in acetonitrile (10 mL) was refluxed for 12 h. The solvent was removed under vacuum and the residue was diluted with water and extracted with ethyl acetate. The organic layer was dried over anhydrous $Na_2SO_4$ and concentrated. The residue was purified by $SiO_2$ column chromatography (elution with ethyl acetate:hexane in 1:3 v:v) to give B in 75% yield. Compound B (400 mg, 1.3 mmol) was refluxed with an ethanolic solution of KOH (30%) for 12 h. The solvent was removed under vacuum and the residue was diluted with water and the pH was adjusted to 5.0 by addition of HCl (1.0 M). The white solid precipitated was filtered with a Buchner funnel, washed with water, and recrystallized from ethanol to give linker $H_2$L in 85% yield. $^1$H NMR (DMSO-$d_6$, 400 MHz): δ=4.57 (d, J=4.5 Hz, 4H), 5.21 (d, J=10.5 Hz, 2H), 5.41 (d, J=16.0 Hz, 2H), 6.02-5.95 (m, 2H), 7.28 (s, 2H), and 12.97 ppm (s, 2H, COOH); $^{13}$C NMR (DMSO-$d_6$, 200 MHz) δ=70.6, 115.5, 118.4, 125.4, 133.2, 151.0, and 167.22 ppm; Elemental Analysis: Anal. Calcd for $C_{14}H_{14}O_6$: C, 60.43; H, 5.07. Found: C, 60.59; H, 5.10.

Example 3

Synthesis of KFUPM-3

Europium nitrate pentahydrate (51 mg, 0.15 mmol), and $H_2$L (42 mg, 0.15 mmol) was dissolve in 8 mL of DMF: EtOH: $H_2O$ (5:2:1) in a glass vial and heated at 80° C. for three days. The reaction mixture was then cooled to room temperature. Small colorless crystals of the product were collected and washed with 3×10 mL of DMF for three days and 3×10 mL of $CH_2Cl_2$ for three days yielding the required KFUPM-3 in 31% yield (related to the Europium salt). IR (KBr, cm$^{-1}$): 3194, 3145, 3001, 2925, 2859, 1571, 1531, 1420, 1369, 1281, 1205, 1104, 1060, 999, 931, 869, 812, 776, 550.

Example 4

Characterization

Single crystal X-ray diffraction (XRD) analysis revealed that KFUPM-3 crystallized in the P-1 (No. 2) space group with unit cell parameters of a=18.0680 (18) Å, b=18.9831 (18) Å, c=22.531 (2) Å, α=106.813 (7)°, β=113.343 (6)°, and γ=96.952 (7)°. Through structural analysis, it was evident that the Eu-based SBU contained two crystallographically independent Eu atoms, which are linked together by a $\mu_3$-O originating from a carboxylate of the BAT linker. Each Eu atom adopts a tricapped trigonal prismatic geometry from the coordination of eight carboxylates and one DMF guest molecule. The dinuclear Eu-oxo SBU is surrounded by six BAT linking units, in which the directionality of these linkers can be reduced down to four total points of extension. As a result, the structure is extended in two-dimensions, adopts the sql topology with a 4^4 tiling (FIG. 1D), and has square-shaped pore windows ~4 Å in size. Due to van der Waals forces, the interlayer spacing of KFUPM-3 is ~3.5 Å.

After solvent exchange and activation, powder X-ray diffraction analysis confirmed phase purity upon comparing the experimental diffraction patterns to that of the diffraction pattern simulated from the single crystal structure. Fourier transform infrared (FT-IR) spectroscopy measurements for KFUPM-3 demonstrated the presence of the characteristic stretching vibrational bands of the allyloxy moiety as well as shifted absorption bands for the carboxylate moiety upon coordination. The thermal stability of KFUPM-3 was proven via thermal gravimetric analysis (TGA), in which there were two main weight losses observed: (i) 8 wt % in the temperature range of 200-300° C., which was assigned to the loss of coordinated DMF and loss of water within the pores; and (ii) 58 wt % in the temperature range of 300-800° C., which was assigned to framework decomposition. The remaining residue (34 wt %) was attributed to $Eu_2O_3$. A $N_2$ adsorption isotherm at 77 K revealed that KFUPM-3 was microporous with a Brunauer-Emmett-Teller surface area of 227 m$^2$ g$^{-1}$ and a pore volume of 0.159 cm$^3$ g$^{-1}$.

Example 5

Crystallization

Figure 5:
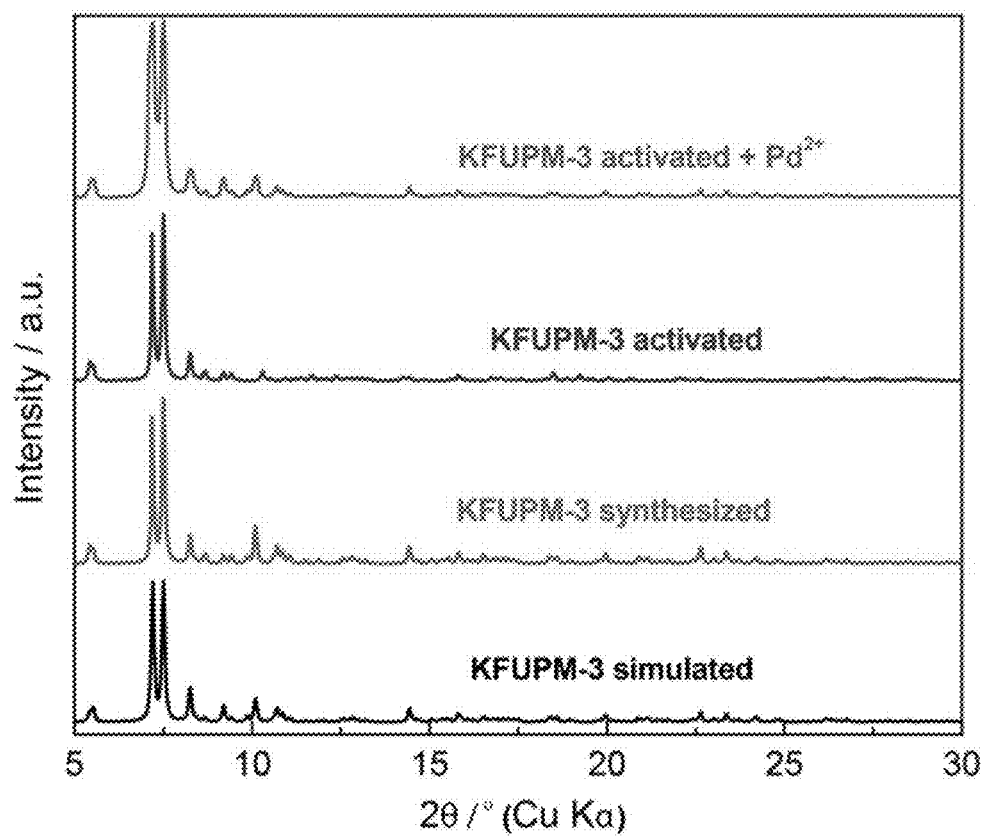
FIG. 5 is powder X-ray diffraction (PXRD) analysis of KFUPM-3 as simulated, synthesized, activated without PdCl$_2$, and activated with the addition of PdCl$_2$.

The powder X-ray diffraction (XRD) of the as-synthesized KFUPM-3 confirmed the phase purity by matching the simulated pattern (FIG. 5) with the corresponding peak at 2θ=5.5, 7.2, 7.5, 8.2, and 9.2.

Figure 1C:
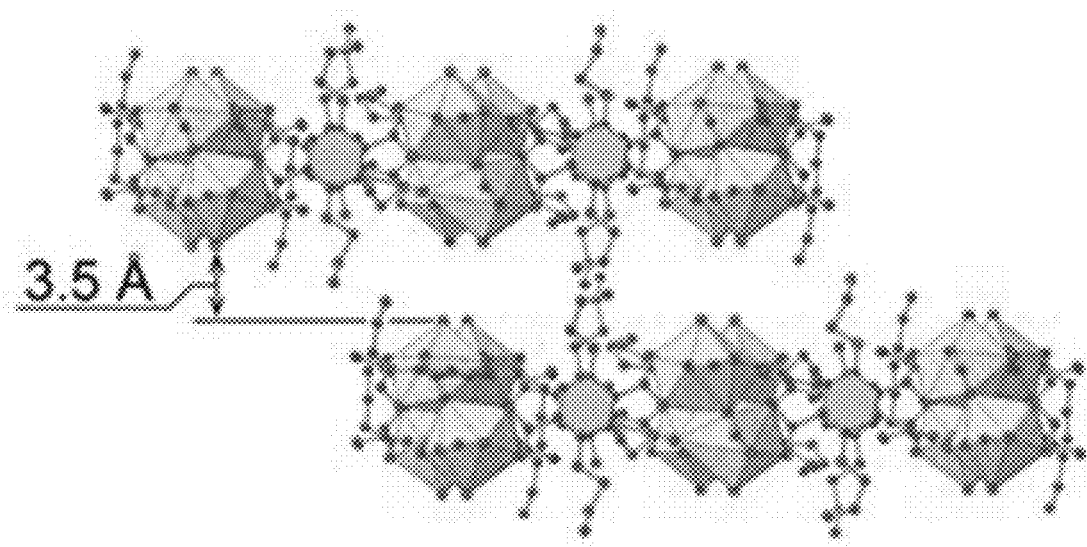
FIG. 1C shows the structure of KFUPM-3 adopting a 2-dimensional layered sql network.
Figure 1D:
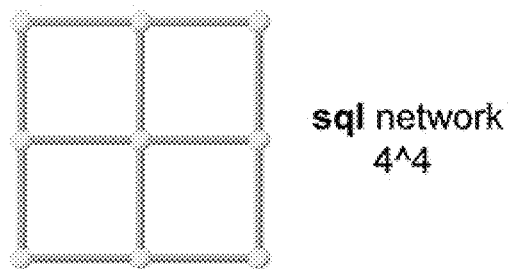
FIG. 1D shows a 2-dimensional sql network.
Figure 6:
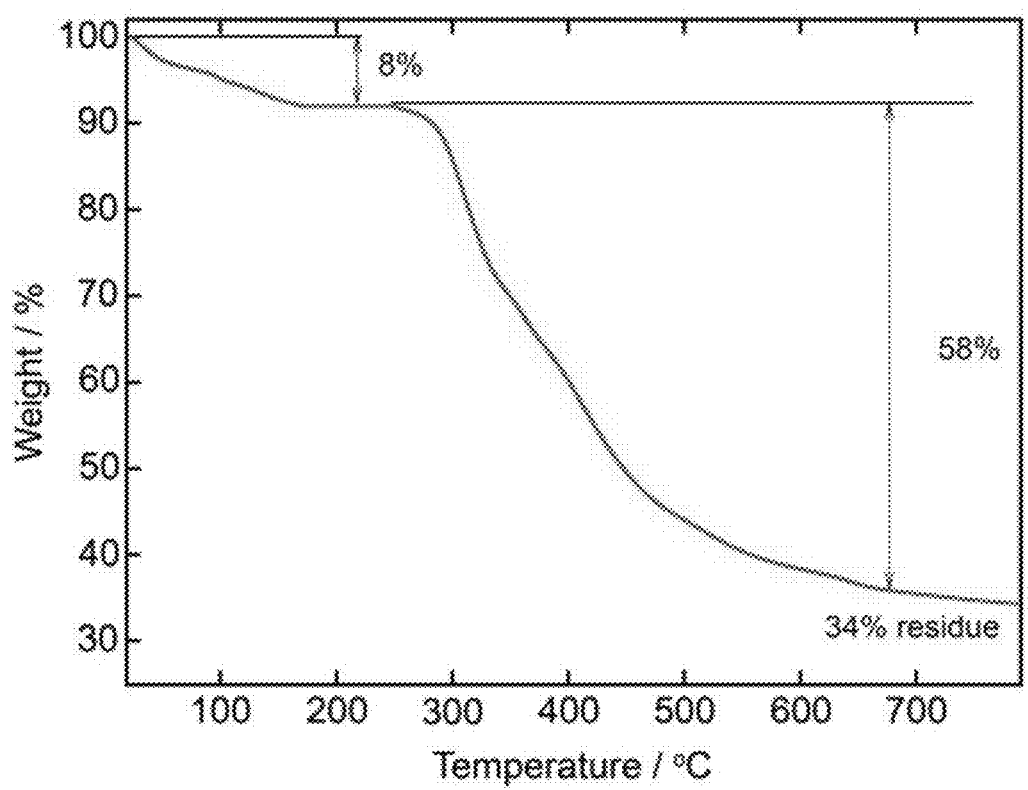
FIG. 6 is a thermal gravimetric analysis (TGA) of KFUPM-3.

KFUPM-3 crystallizes in P-1 space group with the unit cell parameters of a=18.0680 (18) (Å), b=18.9831 (18) (Å), c=22.531 (2) (Å), α=106.813 (7)°, β=113.343 (6)°, and γ=96.952 (7)°. The cluster of Eu contains two (2) Eu atoms which link to each other via the $\mu_3$O of carboxylate functional group of BTA. The Eu-oxo cluster is surrounded by six (6) BTA linking units in which 2 on the top and 2 on the bottom forming the parallel linking units that will be simplified as 2 points. Another 2 points of extension are formed by 2 BTA moieties which incorporate with the parallel coordination to produce 4 points of extension in one node. This node links to others to construct the 2-D layer structure of sql network (4^4 natural tiling). The first layer and the second layer interact to each other via the van der Waals forces and the distance between 2 layers was found to be around 3.5 Å (FIG. 1C). The pore size of KFUPM-3 is 4 Å approximately. Every Eu atom possesses a 9-coordinate environment including 8 of carboxylate linking and one of DMF guest molecule which can be removed to generate the open metal site (OMS) after activation. In order to inspect the thermal stability of the compound, thermogravimetric analysis (TGA) was carried out under air and the temperature was varied from 25 to 800° C. The TGA data (FIG. 6) shows two main weight losses in the curves. The first weight loss of 9.0% was in the temperature range of 200-300° C., corresponding to the loss of the coordinated DMF molecules and water. A further mass loss of 57.0% occurs from 300 to 800° C., which is due to the decomposition of the framework. The final residues were composed of $Eu_2O_3$.

Example 6

Photophysical Properties

After successful structural characterization, the photophysical properties of KFUPM-3 were investigated. As such, the UV-Vis absorption spectrum for KFUPM-3 displayed two peaks, centered at 252 and 336 nm, which resulted from π-π* transitions of the benzene ring and the allylic bond. Optical sensing measurements were then performed using $10^{-2}$ M aqueous solutions of $Pd^{2+}$. Upon slow addition of $Pd^{2+}$ to a suspension of KFUPM-3, the absorbance increased and an additional peak, centered at 276 nm, was observed. This new peak suggested that a possible coordinative interaction was occurring between $Pd^{2+}$ and the allyloxy moiety of KFUPM-3. This response was found to be highly selective as there were no such changes observed when other metal ions (e.g. $Na^+$, $K^+$, $Ca^{2+}$, $Mg^{2+}$, $Sr^{2+}$, $Rb^{2+}$, $Cs^{2+}$, $Fe^{2+}$, $Fe^{3+}$, $Co^{2+}$, $Cu^{2+}$, $Ni^{2+}$, $Zn^{2+}$, $Cd^{2+}$, $Ag^+$, $Al^{3+}$, $Ga^{3+}$, and $Pb^{2+}$) were tested. The stoichiometry of the binding event was then verified by Job's method, which concluded a 1:2 stoichiometric complex formation between KFUPM-3 and $Pd^{2+}$, respectively. See Sanda, S.; Parshamoni, S.; Biswas, S.; Konar, S. Chem. Commun., 2015, 51, 6576-6579, and Li, H.; Fan, J.; Hu, M.; G. Cheng, G.; Zhou, D.; Wu, T.; Song, F.; Sun, S.; Duan, C.; X. Peng, X. Chem.-Eur. J., 2012, 18, 12242, each incorporated herein by reference in its entirety. It is worth noting that the crystallinity of KFUPM-3, characterized by PXRD analysis, was retained after the binding event with $Pd^{2+}$ took place.

Figure 2A:
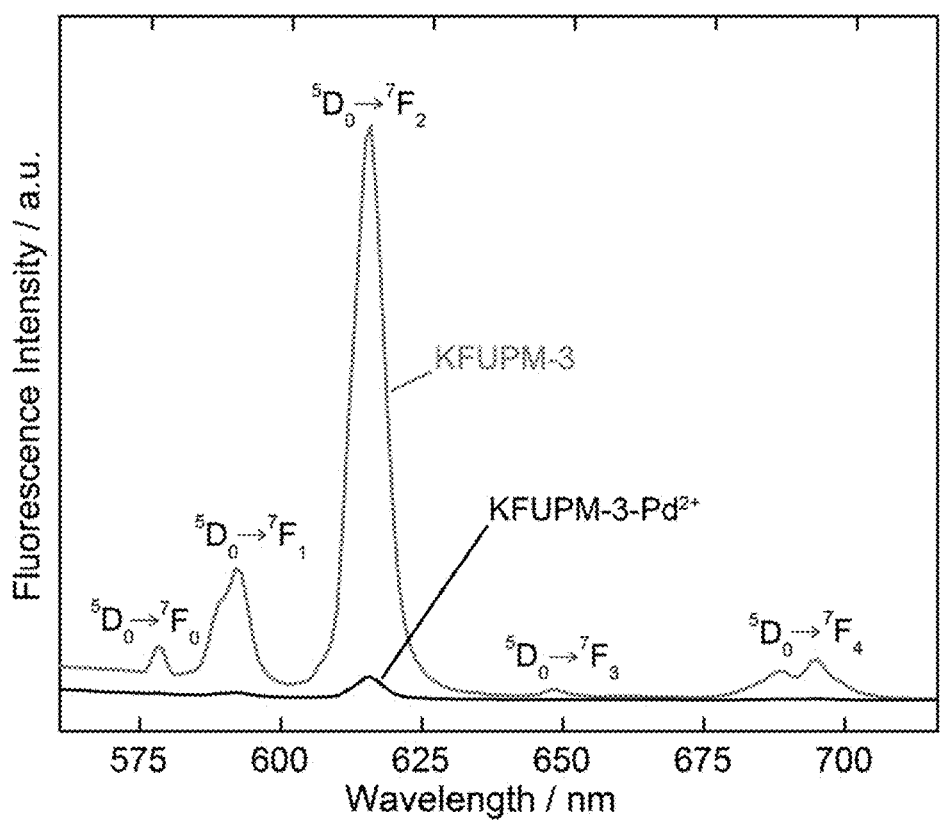
FIG. 2A illustrates the changes in fluorescence spectra of KFUPM-3 upon addition of 200 µL of PdCl$_2$ (10$^{-2}$ M) in water ($\lambda_{ex}$=336 nm).
Figure 2B:
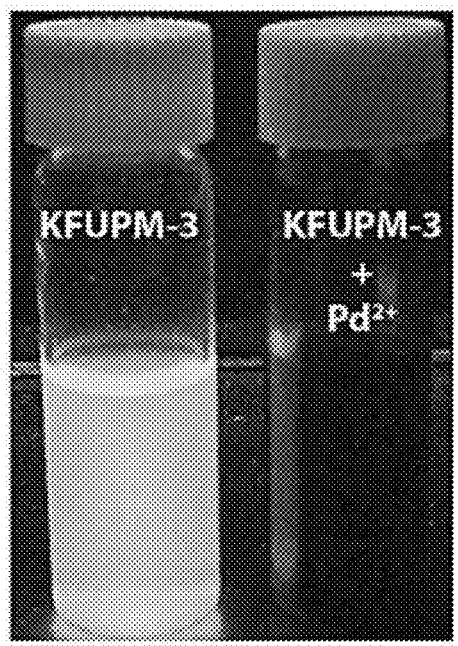
FIG. 2B shows the fluorogenic change from orange (KFUPM-3) to colorless (KFUPM-3-Pd$^{2+}$) upon addition of Pd$^{2+}$ upon irradiation at 365 nm.

Fluorescence spectroscopy measurements were then carried out at an excitation wavelength of 336 nm. At 336 nm, energy transfer occurs from BAT linker excited states to the ground state of the $Eu^{3+}$ ions with fluorescence emissions resulting from f-f transitions. Emission peaks were observed at 578, 592, 616, 648, and 695 nm, which correspond to $^5D_0 \rightarrow ^7F_0$, $^5D_0 \rightarrow ^7F_1$, $^5D_0 \rightarrow ^7F_2$, $^5D_0 \rightarrow ^7F_3$, and $^5D_0 \rightarrow ^7F_4$ transitions, respectively (FIG. 2A). See Binnemans, K.; Coord. Chem. Rev. 2015, 295, 1-45, Tang, Q.; Liu, S.; Liu, Y.; Miao, J.; Li, S.; Zhang, L.; Shi, Z.; Zheng, Z. Inorg. Chem. 2013, 52, 2799-2801, each incorporated herein by reference in their entirety. The most intense fluorescent peak is the $^5D_0 \rightarrow ^7F_2$ transition originating from a $Eu^{3+}$ with anti-inversion symmetry. It is also noted that the emission of the BAT linker does not appear in the emission spectrum of KFUPM-3, which indicates that an antenna effect is present. Finally, the absolute quantum yield for KFUPM-3 was calculated from the integrated sphere to be 0.48 and the CIE coordinates, obtained from the chromaticity diagram, agree with the experimentally derived emission results.

Figure 3:
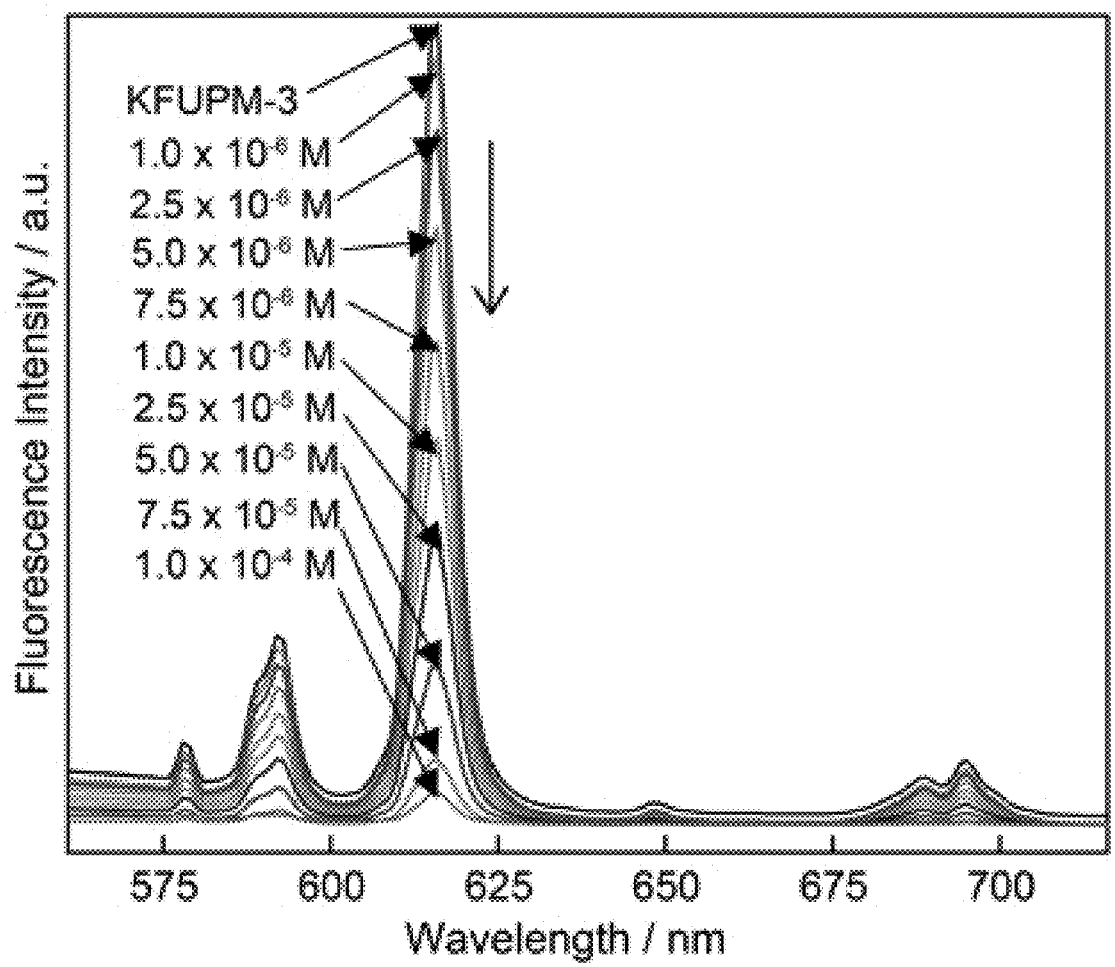
FIG. 3 illustrates the changes in the emission spectrum of KFUPM-3 in water upon incremental addition of PdCl2 ($\lambda_{ex}$=336 nm).
Figure 4:
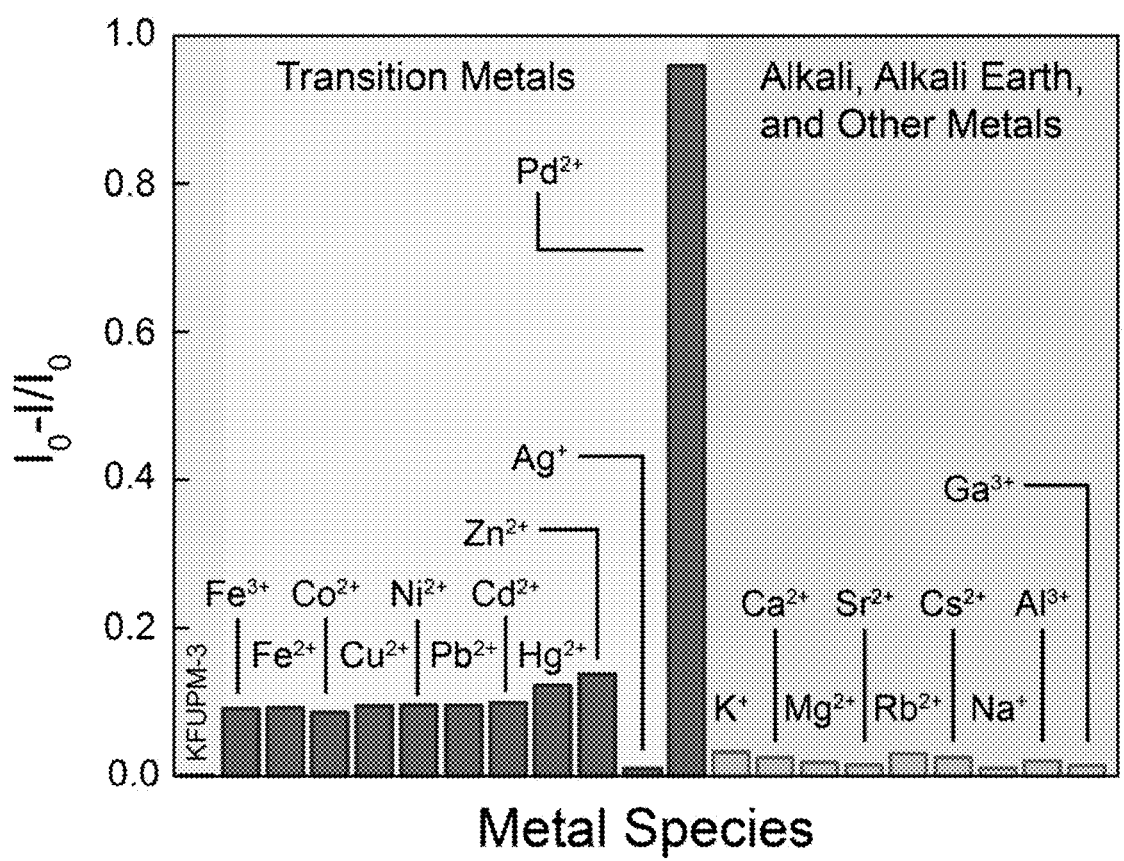
FIG. 4 illustrates the change in the normalized fluorescence emission of KFUPM-3 in water upon addition of 200 μL, of different metal cations ($10^{-2}$ M; $\lambda_{ex}$=336 nm).

In order to understand the sensitivity of KFUPM-3's chemosensing properties, changes to the fluorescence emission intensity were investigated as a function of increasing $Pd^{2+}$ concentration. As expected, fluorescence was quantitatively quenched upon exposure to increasing concentrations of $Pd^{2+}$ and was observed to be completely quenched when a 2:1 $Pd^{2+}$:KFUPM-3 molar ratio was achieved. This complete quenching indicates that full complexation was realized between $Pd^{2+}$ and the two allyloxy moieties on the BAT linker (FIGS. 2A and 3). It is noted that $Pd^{2+}$ complexation within KFUPM-3's channels are expected to perturb the electronic structure of the BAT linker, which affects the excited state of the linkers. This perturbation then impacts the sensitization of the $Eu^{3+}$ emissive state by prohibiting energy transfer from the linkers to the $Eu^{3+}$ SBUs, which consequently leads to quenching of the fluorescence. The quenching efficiency was then interpreted by calculating the Stern-Volmer constant. See Sanda, S.; Parshamoni, S.; Biswas, S.; Konar, S. Chem. Commun., 2015, 51, 6576-6579, Li, H.; Fan, J.; Hu, M.; G. Cheng, G.; Zhou, D.; Wu, T.; Song, F.; Sun, S.; Duan, C.; X. Peng, X. Chem.-Eur. J., 2012, 18, 12242, each incorporated herein by reference in their entirety. On the basis of the titration curve, shown in FIG. 3, the Stern-Volmer constant, $K_{sv}$, was calculated to be 7.8× $10^4$, which is comparable to values obtained for other suspension-based $Pd^{2+}$ chemosensors. The sensitivity of KFUPM-3 towards $Pd^{2+}$ was demonstrated based on the calculated detection limit. For KFUPM-3, this detection limit was 44 ppb, which is significantly lower than the 5-10 ppm threshold for palladium in pharmaceutical products. See Palladium, Environmental Healthy Criteria Series 226, Inter-national Programme on Chemistry Safety, World Health Organization, Geneva, Switzerland, 2002, incorporated herein by reference in its entirety. To assess changes in the emission spectra in the presence of metal contaminants, KFUPM-3 was again immersed in solutions of different metal ions. As shown in FIG. 4, emission remained for all metal ions tested, whereas the emission was quenched when $Pd^{2+}$ was in the presence of KFUPM-3. Again, this demonstrates that a highly selective chemosensing process is occurring for KFUPM-3 with $Pd^{2+}$.

Competition experiments were then carried out in order to explore the possibility of using KFUPM-3 as a practical ion-selective ($Pd^{2+}$) fluorescent chemosensor. In these studies, KFUPM-3 was first exposed to 200 µL of various competitor metal ions ($10^{-2}$ M), at which time 200 µL of $Pd^{2+}$ was then added. Fluorescence emission spectroscopy exhibited no interference in the emission when competitor metal ions were present with $Pd^{2+}$. For environmental and physiological applications, chemosensors also must operate in media with widely varying pHs. The emission properties and the crystallinity of KFUPM-3 were effectively maintained within a pH range of 6.0-10.0. Beyond this range, the structure of KFUPM-3 decomposes, as proven by PXRD analysis, and the emission properties are lost. The emission response of KFUPM-3 was also evaluated in the presence of different palladium species with varying oxidation states: $PdCl_2$, $Pd(PPh_3)_4$, $Pd(OAc)_2$, $PdCl_2(PPh_3)_2$, $(NH_4)_2PdCl_6$ and $Pd_2(dba)_3$. As such, there were negligible differences observed for the emission response of KFUPM-3 towards these differing palladium species. Since no additional reagents were added during the analysis to alter the oxidation states of these species, it is presumed that KFUPM-3 can interact with palladium irrespective of the oxidation state.

Finally, the reusability of KFUPM-3 as a practical chemosensor was demonstrated. In a typical experiment, a dispersion of KFUPM-3-$Pd^{2+}$ (KFUPM was pre-exposed to $Pd^{2+}$) in aqueous media was treated with 0.1 M ethylenediaminetetraacetic acid. Fluorescence spectroscopy was then performed and an emission signal, with a maximum at 616 nm, was observed to be recovered over the course of four consecutive cycles. This study powerfully demonstrates that the MOF-$Pd^{2+}$ coordinative binding is chemically reversible as opposed to an irreversible cation-catalyzed reaction. Moreover, the diffraction pattern of KFUPM-3 showed that the crystallinity of the material was maintained.

Example 7

Optical Sensing Properties

The optical sensing properties of KFUPM-3 were investigated in an aqueous system. The emission studies were performed in an aqueous system by using $10^{-2}$ M solutions of the analytes. Initial studies on the UV-vis absorption and fluorescent emission revealed that KFUPM-3 showed selectivity toward $Pd^{2+}$ ions under aqueous condition.

Figure 7:
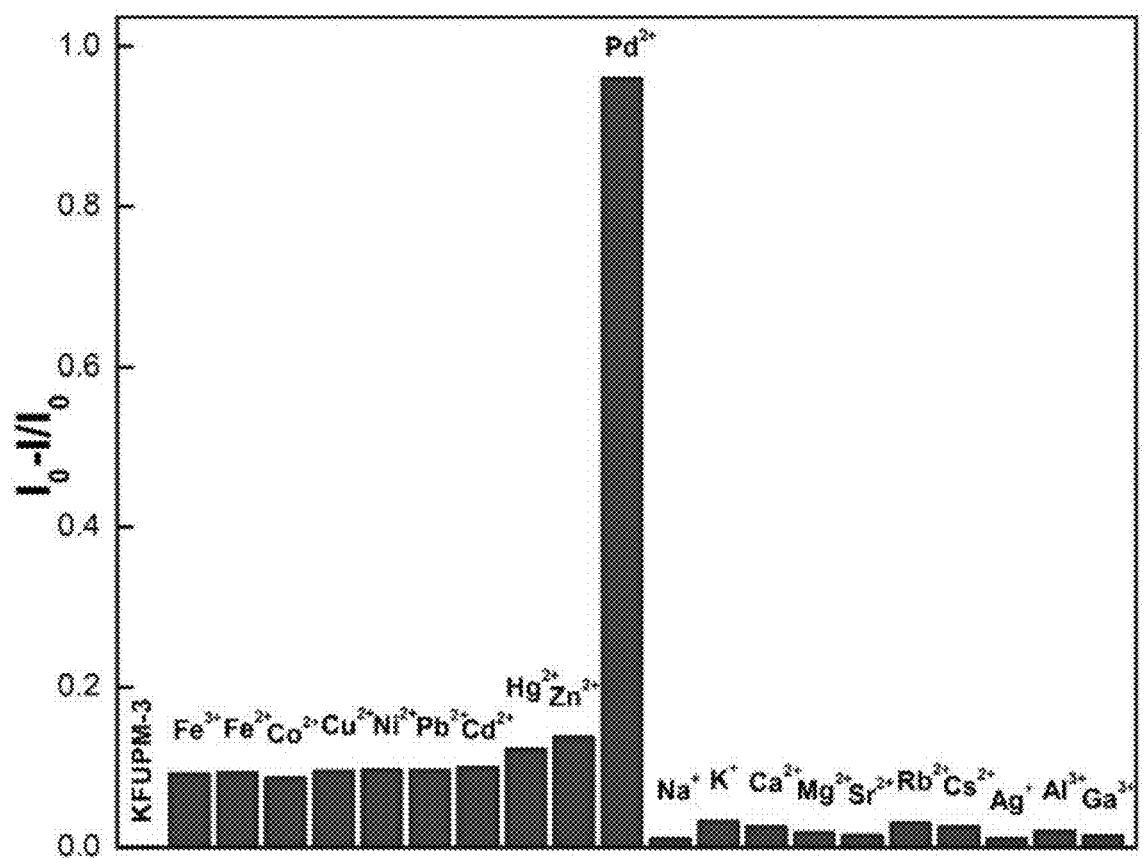
FIG. 7 shows the change in the normalized fluorescence emission ($\lambda_{ex}$=336 nm) of KFUPM-3 in water upon addition of 200 μL of different metal cations (each $10^{-2}$ M).

The emission spectra of KFUPM-3 excited at 336 nm is due to the energy transfer from the excited energy level of the organic ligand to the ground state of the lanthanide ions, that results in the sharp and strong emission of the $Eu^{3+}$. This antenna effect reveals well-resolved magnified luminescence of the f-f transitions, attributed to the energy transfer from ligands to $Eu^{3+}$ ions. Characteristic transitions of the $Eu^{3+}$ ion are also evident with peaks at 578, 592, 616, 648, and 695 nm, which could be attributed to $^5D_0 \rightarrow ^7F_0$, $^5D_0 \rightarrow ^7F_1$, $^5D_0 \rightarrow ^7F_2$, $^5D_0 \rightarrow ^7F_3$, and $^5D_0 \rightarrow ^7F_4$ transitions, respectively. The $^5D_0 \rightarrow ^7F_2$ transition has maximum luminescent intensity at the 616 nm, as originated to the low symmetry of the $Eu^{3+}$, demonstrating that the incorporated $Eu^{3+}$ is located at anti inversion symmetry (FIG. 3). It is also noted that the emission of the ligand $H_2L$ does not appear in the emission spectrum of the KFUPM-3, which indicates the presence of the antenna effect. In order to check the selectivity of the KFUPM-3 with a different cation it was immersed in the $10^{-2}$ M solution of different cations, both alkaline earth and transitional metals (FIG. 7).

Figure 8:
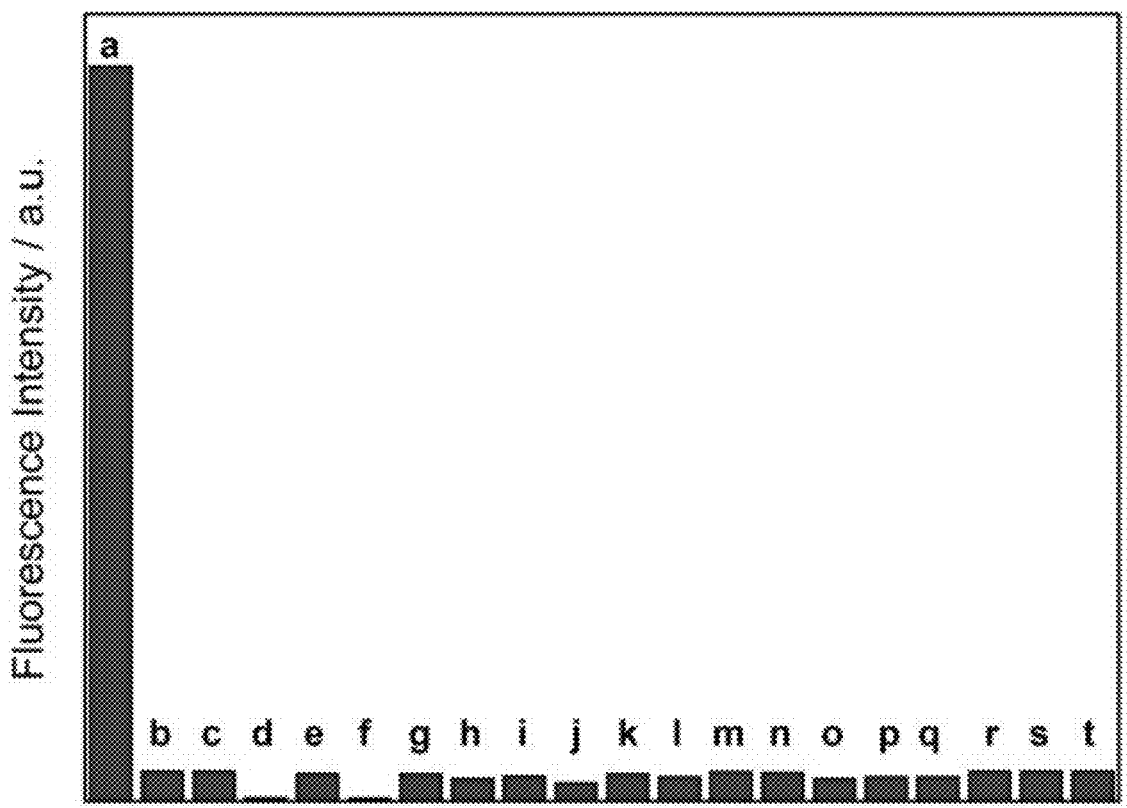
FIG. 8 shows the competitive metal ion selectivity of KFUPM-3: Bars indicate the fluorescence intensity (336 nm excitation, 616 nm emission). Salts of various metal ions ($10^{-2}$ mM each) were added to KFUPM-3 and Pd$^{2+}$ ($10^{-2}$ M) (a) KFUPM-3 only, (b) Ag$^+$+Pd$^{2+}$, (c) Pd$^{2+}$+Pd$^{2+}$, (d) Zn$^{2+}$+Pd$^{2+}$, (e) Mg$^{2+}$+Pd$^{2+}$, (f) Fe$^{3+}$+Pd$^{2+}$, (g) K$^+$+Pd$^{2+}$, (h) Co$^{2+}$+Pd$^{2+}$, (i) Al$^{3+}$+Pd$^{2+}$, (j) Fe$^{2+}$+Pd$^{2+}$, (k) Na$^+$+Pd$^{2+}$, (l) Cd$^{2+}$+Pd$^{2+}$, (m) Sr$^{2+}$+Pd$^{2+}$, (n) Rb$^+$+Pd$^{2+}$, (o) Cu$^{2+}$+Pd$^{2+}$, (p) Ni$^{2+}$+Pd$^{2+}$, (q) Hg$^{2+}$+Pd$^{2+}$, (r) Ga$^{3+}$+Pd$^{2+}$, (s) Cs$^+$+Pd$^{2+}$, and (t) Ca$^{2+}$+Pd$^{2+}$ in water.
Figure 9:
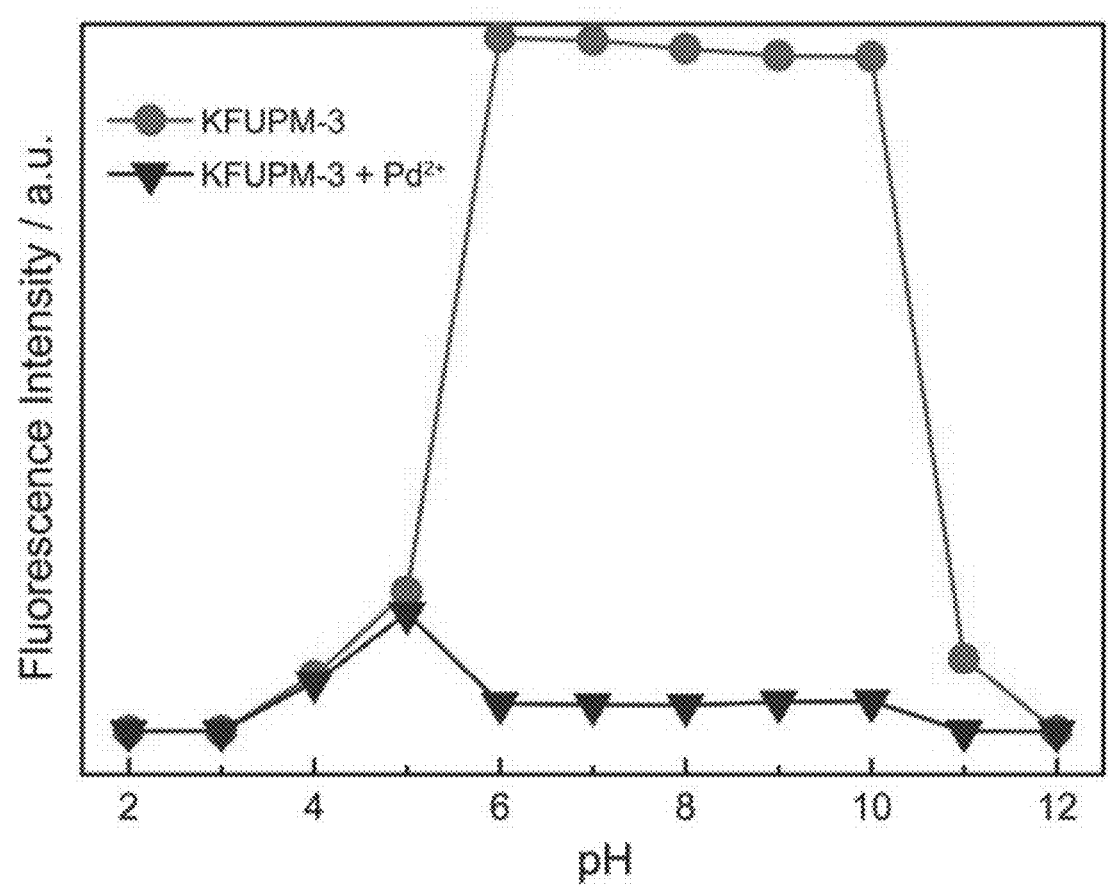
FIG. 9 shows the effect of pH on the emission intensities at 616 nm of KFUPM-3, in H$_2$O ($\lambda_{ex}$=336 nm).

The study of the photoluminescence properties of these suspensions showed that none of the metal produces any quenching or switch off fluoroionophoric property as produced by the $Pd^{2+}$. The changes in fluorescence intensity of KFUPM-3 were investigated by the incremental addition of $Pd^{2+}$ ion, which resulted in quantitative quenching (FIG. 3). The quenching efficiency can be interpreted by calculating the Stern-Volmer constants ($K_{sv}$). See S. Cai, Y. Lu, S. He, F. Wei, L. Zhaoab and X. Zeng, Chem. Commun., 2013, 49, 822, each incorporated herein by reference in their entirety. On the basis of the titration curve in FIG. 3, the Stern-Volmer constant $K_{sv}$ is calculated to be $7.8 \times 10^4$ which is comparable with the values obtained from the other suspension based $Pd^{2+}$ sensors. Complexation with the $Pd^{2+}$ into the MOF channels through binding with the allyl group is expected to perturb the electronic structure of the ligand that effects the excited state of the ligands, and this in turn effects the sensitization of the emissive state of the $Eu^{3+}$ by inhibition of the energy transfer from ligands to $Eu^{3+}$ ions thus resulting in quenching of the fluorescence. The detection limit for $Pd^{2+}$ calculated was found to be 44 ppb, which is quite lower than the low residue threshold of 5-10 ppm of palladium in drugs. To explore the possibility of using KFUPM-3 as a practical ion-selective fluorescent chemosensor for $Pd^{2+}$, competition experiments were carried out, in which KFUPM-3 was first mixed with 200 μL of various competing metal ions followed by adding 200 μL of $Pd^{2+}$. Fluorescence emission spectroscopy showed that a wide variety of common coexisting metal ions mostly exhibited no obvious interference in the detection of $Pd^{2+}$ (FIG. 8). For environmental and physiological applications, chemosensors should operate in a wide range of pH. For KFUPM-3 the emission and the crystallinity study showed that it can be effectively used within the pH range of 6.0-10.0 (FIG. 9). Beyond this range, it is ineffective due to the destruction of the crystallinity of the MOF as obtained from the PXRD at different pH.

Figure 10:
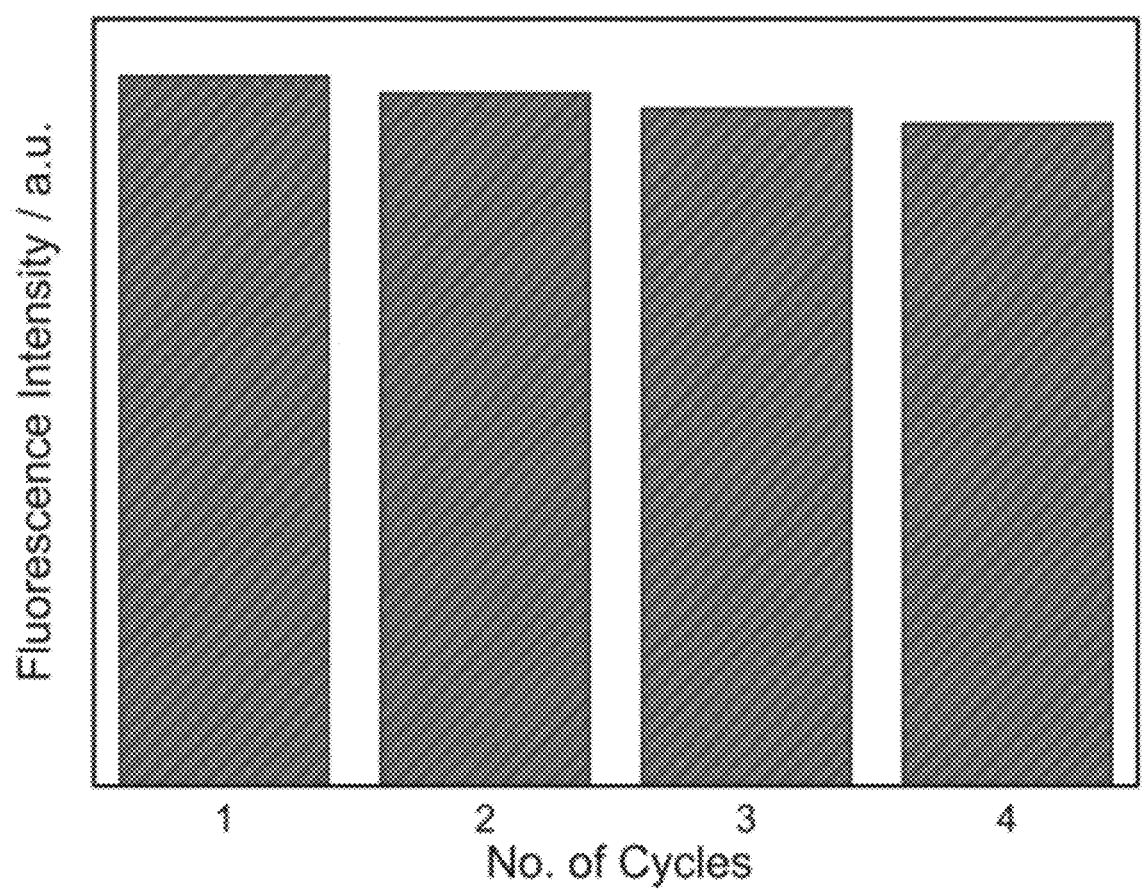
FIG. 10 shows the fluorescence intensity after regeneration of KFUPM-3 from KFUPM-3+Pd$^{2+}$ by treating with EDTA for 4 cycles.

The absolute quantum yield of the KFUPM-3 calculated from the integrate sphere using a liquid sample holder at room temperature was found to be 0.48. The chemical reversibility of the KFUPM-3 upon addition of $Pd^{2+}$ was also investigated in order to study the reusability of the sensor. The aqueous dispersion of KFUPM-3+ $Pd^{2+}$ formed was treated with 0.1 M EDTA solution and a fluorescence signal with a maximum at 616 nm was completely recovered with each of four more cycles, demonstrating the binding is chemically reversible and not a cation-catalyzed reaction (FIG. 10). Moreover, the PXRD of the material after each cycle also showed that the crystallinity is maintained.

A new fluorescent Europium-based MOF (KFUPM-3) was developed, containing the linking unit, 2,5-bis(allyloxy) terephthalate sensitive and selective to palladium. As such, KFUPM-3 was demonstrated to act as a highly selective, ultrasensitive, reversible, and fluorogenic chemosensor for different palladium species under aqueous conditions. The responsiveness is due, in large part, to coordinative binding of palladium to the allyloxy moieties of the BAT linker, which perturbs the electronic structure of the linker and, thus, quenches the fluorescence of the MOF. The KFUPM-3 utilizes strong coordination of palladium cations with the alkene (—CH=CH—) moieties of the bis(allyloxy)terephthalate and the antenna effect of the Europium ion for the sensing. KFUPM-3 exhibits an "on-off" type of fluoroionophoric switching and generates an absolute quantum yield of 0.48, a very low detection limit of 44 ppb of $Pd^{2+}$, and a Stern-Volmer constant of $7.8 \times 10^4$. The new Eu-MOF based on Europium metal cluster and an allyl linking unit, 2,5-bis (allyloxy)terephthalate, termed KFUPM-3, was successfully prepared using a facile solvothermal method and characterized by single X-ray diffraction (SXRD), powder X-ray diffraction (PXRD), nitrogen physisorption analysis, thermogravimetric analysis (TGA) and Fourier-transform infrared spectroscopy (FT-IR). Selective changes both in the absorption and emission spectrum of KFUPM-3 were observed upon treatment with palladium in an aqueous solution which was attributed to the inhibition of the antenna effect due to the binding of the palladium in the aqueous solution. KFUPM-3 has an absolute quantum yield of 0.48, and a very low detection limit of 44 ppb of $Pd^{2+}$.

The invention claimed is:
1. A method of detecting $Pd^{2+}$ in an aqueous solution, the method comprising:
   mixing an Eu-based metal organic framework (Eu-MOF) with the aqueous solution to form a solution mixture, wherein the Eu-MOF comprises:
   $Eu^{3+}$ ion clusters, each $Eu^{3+}$ ion cluster comprising two $Eu^{3+}$ ions, wherein each $Eu^{3+}$ ion cluster is coordinated with a total of 6 linkers, and wherein each linker has a dicarboxylic acid and two alkene groups;

measuring a fluorescence emission intensity of the solution mixture while irradiating the solution mixture with a wavelength in a range of 320-350 nm; and comparing the fluorescence emission intensity to a second fluorescence emission intensity of a substantially similar solution mixture that does not contain $Pd^{2+}$.

2. The method of claim 1, wherein the alkene groups are part of allyloxy groups.

3. The method of claim 2, wherein the linker is 2,5-bis(allyloxy)terephthalic acid.

4. The method of claim 1, wherein the linker is present in the Eu-MOF with a weight percent in a range of 55-75 wt %, relative to a total weight of the Eu-MOF.

5. The method of claim 1, wherein each $Eu^{3+}$ ion cluster is coordinated in a 2D layered structure.

6. The method of claim 5, wherein the 2D layered structure has an interlayer spacing in a range of 3.2-3.8 Å.

7. The method of claim 1, wherein the Eu-MOF has an average pore size in a range of 3.5-4.5 Å.

8. The method of claim 1, wherein the Eu-MOF has a pore volume in a range of 0.10-0.20 cm³/g.

9. The method of claim 1, wherein the Eu-MOF has a BET surface area in a range of 200-250 cm²/g.

10. The method of claim 1, wherein the Eu-MOF has an absolute quantum yield in a range of 0.40-0.55.

11. The method of claim 1, wherein the Eu-MOF is present in the solution mixture at a concentration in a range of 1-100 mM.

12. The method of claim 1, wherein the solution mixture has a pH in a range of 6.0-10.0.

13. The method of claim 1, having a $Pd^{2+}$ limit of detection in a range of 10-60 ppb.

14. The method of claim 1, wherein the solution mixture further comprises at least one metal ion selected from the group consisting of $Ag^+$, $Pb^{2+}$, $Zn^{2+}$, $Mg^{2+}$, $Fe^{3+}$, $K^+$, $Co^{2+}$, $Al^{3+}$, $Fe^{2+}$, $Na^+$, $Cd^{2+}$, $Sr^{2+}$, $Rb^+$, $Cu^{2+}$, $Ni^{2+}$, $Hg^{2+}$, $Ga^{3+}$, $Cs^+$, $Ca^{2+}$, $Pt^{2+}$, $Ir^{3+}$, and $Rh^{3+}$.

15. The method of claim 1, wherein the solution mixture comprises the at least one metal ion at a concentration in a range of 1-100 mM.

16. The method of claim 1, wherein the fluorescence emission intensity of the solution mixture is measured at a wavelength in a range of 605-630 nm.

17. The method of claim 1, further comprising removing the Eu-MOF from the solution mixture to produce a recovered Eu-MOF;

mixing the recovered Eu-MOF with a solution comprising a metal chelator to produce a chelating solution;

separating the Eu-MOF from the chelating solution to produce a renewed Eu-MOF, and reusing the renewed Eu-MOF for the detection of $Pd^{2+}$.

18. The method of claim 17, wherein the metal chelator is present in the chelating solution at a concentration in a range of 0.05-0.5 M.

19. The method of claim 17, wherein the metal chelator is EDTA.

20. The method of claim 17, wherein the renewed Eu-MOF is reused at least 3 times, and wherein the renewed Eu-MOF has a fluorescence intensity that is at least 90% of the Eu-MOF fluorescence intensity before the mixing.

* * * * *